US008110354B2

(12) United States Patent
Oaks et al.

(10) Patent No.: US 8,110,354 B2
(45) Date of Patent: *Feb. 7, 2012

(54) USE OF *SHIGELLA* INVAPLEX TO TRANSPORT FUNCTIONAL PROTEINS AND TRANSCRIPTIONALLY ACTIVE NUCLEIC ACIDS ACROSS MAMMALIAN CELL MEMBRANES IN VITRO AND IN VIVO

(75) Inventors: Edwin V. Oaks, Gambrills, MD (US); Robert W. Kaminski, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/563,794

(22) Filed: Sep. 21, 2009

(65) Prior Publication Data

US 2010/0119543 A1 May 13, 2010

Related U.S. Application Data

(63) Continuation of application No. 10/994,463, filed on Nov. 23, 2004, now Pat. No. 7,632,659.

(60) Provisional application No. 60/524,639, filed on Nov. 25, 2003.

(51) Int. Cl.
*C12Q 1/68* (2006.01)
*C12N 5/00* (2006.01)

(52) U.S. Cl. ........ 435/6.1; 435/6.15; 435/6.18; 435/325

(58) Field of Classification Search ........................ None
See application file for complete search history.

(56) References Cited

U.S. PATENT DOCUMENTS

| | | | | |
|---|---|---|---|---|
| 6,245,892 | B1 * | 6/2001 | Oaks et al. | 530/350 |
| 7,632,659 | B2 * | 12/2009 | Oaks et al. | 435/69.1 |
| 2001/0009957 | A1 | 7/2001 | Oaks et al. | |

FOREIGN PATENT DOCUMENTS

| | | |
|---|---|---|
| WO | 00/23462 | 4/2000 |
| WO | 02/094190 | 11/2002 |

OTHER PUBLICATIONS

"Development of invaplex as an vitro transfection reagent (Ligocyte Pharmaceuticals),"Montana Department of Commerce, Online! Aug. 23, 2004, URL:http://www.commerce.state.mt.us.

"Internalization of invaplex isolated from *Shigelia flexneri* and co-localization with intracellular organelles", Kaminski et al., Abstracts of the 104$^{th}$ General Meeting of The American Society for Microbiology, vol. 1, May 23, 2004, p. B32.

"Delivery of proteins and nucleic acids into mammalian cells with *Shigella flexneri* invaplex", Kaminski et al., Abstracts of the 104$^{th}$ General Meeting of The American Society for Microbiology, vol. 1, May 23, 2004, p. B36.

* cited by examiner

*Primary Examiner* — Albert Navarro
(74) *Attorney, Agent, or Firm* — Elizabeth Arwine

(57) ABSTRACT

The in vivo and in vitro use of Invaplex to transport materials, including functional proteins and biologically active nucleic acids, across eukaryotic cell membranes. The eukaryotic cells include a variety of cell types, e.g. insect, reptile, fish, mammal and tumor cells. The suitable materials for transport include biochemicals such as reporter molecules, antibiotics, biopharmaceuticals and carbohydrates including polysaccharides, lipopolysaccharides, polynucleotides, such as DNA and RNA, and glycoproteins and proteins including antigens, enzymes, antibodies, receptors and hormones. In addition, Invaplex enhances the immune response to DNA vaccines and also can function by itself as a vaccine against shigellosis.

12 Claims, 16 Drawing Sheets

USE OF *SHIGELLA* INVAPLEX TO TRANSPORT FUNCTIONAL PROTEINS AND TRANSCRIPTIONALLY ACTIVE NUCLEIC ACIDS ACROSS MAMMALIAN CELL MEMBRANES IN VITRO AND IN VIVO

This application is a continuation of application Ser. No. 10/994,463, filed Nov. 23, 2004, now U.S. Pat. No. 7,632, 659, which is based on provisional application Ser. No. 60/524,639 filed on Nov. 25, 2003. The content of the provisional application are expressly incorporated herein by reference.

FIELD OF THE INVENTION

The present invention provides for the in vivo and in vitro use of Invaplex to transport materials including functional proteins and biologically active nucleic acids across mammalian cell membranes compositions. The present invention also relates to adjuvants, immunogenic compositions and methods useful for polynucleotide-based vaccination.

BACKGROUND OF THE INVENTION

Invaplex as a Vaccine

The pathogenesis of *Shigella* spp. is attributed to this organism's ability to invade, replicate intracellularly, and spread intercellularly within the colonic epithelium. Several highly conserved, virulence plasmid-encoded proteins, called the invasion plasmid antigens (IpaA, IpaB, IpaC, and IpaD) (1), are essential participants in the invasion process. Upon contact or attachment to host cells, the *Shigella* invasins are released (22) by a type III secretion apparatus (8) and induce a phagocytic event resulting in engulfment and internalization of the bacterium by the host cell (7). The active components include an IpaB:IpaC complex that integrates into the host cell membrane, forming a channel by which other *Shigella* proteins gain entry into the host cell (16).

Recently, we have isolated an invasin protein-LPS complex from intact, virulent *Shigella* cells (20). The invasin complex or Invaplex is the subject of several issued or pending WRAIR patents (11-14). The invasin complex (Invaplex) binds to surfaces of epithelial cells and quickly becomes internalized, presumably by an endocytic process (Oaks and Kaminski, unpublished data). The ability to bind to a eukaryotic host cell surface and induce a phagocytic event indicates that the Invaplex maintains an active, native virulence structure similar to that found on the surface of invasive *Shigella*. In fact, many of the key, antigenic components found in Invaplex 24 and Invaplex 50 (see below) are located on the *Shigella* surface. These antigens include IpaB, IpaC, IpaD and LPS (all of which are present in both Invaplex 24 and Invaplex 50) and also the newly described protein antigens 72 kDa, 84 kDa, and a 60 kDa protein found exclusively in Invaplex 50 (Oaks & Turbyfill, unpub data). More recently a highly purified form of Invaplex (HP Invaplex) has been isolated by size-exclusion chromatography (SEC). The HP Invaplex 24 consists of IpaB, IpaC and LPS and has an estimated mass of about 1 MDal. Experiments in mice have determined that the *S. flexneri* HP-Invaplex 24 or HP-Invaplex 50 offer enhanced immunogenicity and efficacy over the parent Invaplex indicating that the active components of Invaplex are, at a minimum, IpaB, IpaC and LPS.

The ability to isolate a putative native surface structure such as Invaplex, which exhibits activities and immunogenicity similar to invasive shigellae, has significant implications in vaccine design and development. First, the putative native structure may enhance delivery to the appropriate portal of entry (M-cells), similar to that targeted by live-attenuated vaccine strains. In the case of Invaplex, this has allowed the use of relatively small doses for intranasal immunization due to its delivery efficiency. Similar to live, attenuated vaccines, immunization with the isolated subcellular, native Invaplex structure that contains all known *Shigella* antigens results in an immune response equivalent to that produced during natural infection, including recognition of epitopes found only in native structures. The immunity stimulated by Invaplex is highly protective in mice and guinea pigs (12, 20).

Invaplex as an Adjuvant

The delivery of antigens in a manner, which safely stimulates a protective mucosal immune response, is critical to the successful development of enteric vaccines. As an alternative to live attenuated vaccines, which are often difficult to construct, standardize and deliver without the risk of side effects, subunit vaccines offer the promise of chemically defined, well-standardized products. Unfortunately, the rapid increase in potential subunit vaccines arising from recombinant, synthetic, or subunit purifications, including both protein and DNA vaccines, has outpaced the ability to deliver these novel vaccines safely and effectively. A major obstacle has been the failure to develop an adjuvant, which effectively stimulates the mucosal immune system in a safe, nontoxic manner. One highly effective mucosal adjuvant is cholera toxin (CT), another is *E. coli* heat-labile enterotoxin (LT); unfortunately, both are extremely toxic molecules that require substantial detoxification by genetic manipulations. Before genetically modified forms of CT or LT become available as adjuvants for human use, they will require extensive safety testing.

A unique property of the Invaplex is that it enhances the immune response to substances that are not very immunogenic (11). The adjuvanticity of Invaplex has been demonstrated with several proteins including ovalbumin, the recombinant Sta56 (56K) protein of *Orientia tsustsugamushi*, the FlaA protein of *Campylobacter jejuni*, colonization factors of enterotoxigenic *E. coli* and the PA (protective antigen) of *Bacillus anthracis* (Oaks and Kaminski, unpublished data). The immunogenicity and adjuvanticity of the Invaplex is likely due to its ability to target and induce uptake by immune cells, possibly M cell equivalents in the mucosa. Stimulation of a mucosal immune response often requires uptake of the antigen or pathogen by M cells in the gut or comparable cells in other mucosal tissue. The M cells lie over an area of cells called the mucosa associated lymphoid tissue (Peyer's patches in the gut). Upon uptake of antigen, the M cell is capable of translocating the antigen to the lymphoid tissue consisting of lymphocytes, macrophages, and dendritic cells. These cells serve to present the antigen to antigen-specific lymphocytes resulting in stimulation, expansion, and expression of specific immune effectors. In the mucosa, this process leads to the development of IgA-producing B cells.

The adjuvanticity of Invaplex is likely mediated by IpaB and IpaC, which are crucial virulence proteins involved in the invasiveness of shigellae. Very little is known about the effect Invaplex has on host cells.

DNA Transfection and DNA Vaccines.

The process of delivering transcriptionally active DNA into eukaryotic cells is called transfection. The result of transfection is heterologous gene expression in vitro or in vivo. Transfection is often used as a means to study the function of specific proteins expressed in the transfected cell. Although physical methods such as microinjection and electroporation can be used to shuttle DNA into eukaryotic cells, methods more amenable to in vivo work have been developed. Transfection of cells in vivo has extended the in vitro functional analysis into live animals and has also allowed the immunogenicity of the expressed protein to be evaluated if the levels of antigen expression in vivo are high enough. One advantage of DNA vaccines is that the DNA can be produced easily and is relatively inexpensive (2). Optimal expression of the genes of interest often requires genetic customization of the cloned gene. In DNA vaccines, in particular those delivering bacterial antigen genes, a cloned eukaryotic promoter, such as the cytomegalovirus (CMV) promoter, is used to drive expression of the antigen gene. Other considerations of the antigen genes are codon usage (certain bacterial genes may be suboptimal for eukaryotic expression) and the stability of the DNA construct in particular during delivery at mucosal sites. Many DNA vaccines have been delivered intramuscularly or intradermally with the gene gun (21). Mucosal delivery of DNA vaccines is difficult due to the likely degradation of the DNA upon exposure to enzymes and harsh conditions in the mucosa. Mucosal DNA delivery systems include liposomes (4, 6), microparticles (3) and live bacterial vectors (5). None of these mucosal delivery systems use a native acellular bacterial product, such as Invaplex, to deliver the DNA.

Protein Delivery Systems

In most cases a successful DNA delivery system (transfection reagent) is somewhat universal in that it will work, with most DNA molecules due to the relatively similar biochemical (negatively charged nucleic acid) structure of DNA. Proteins, on the other hand, have a much more varied biochemical structure, in that their net charge, conformation, hydrophilicity, and size are highly variable. This creates a different problem for transporting functional proteins into host cells. Strategies used to transport proteins into cells include the use of cationic lipids (23) or specialized peptides consisting of protein transduction domains (17) or membrane transport signals (15). The specialized peptides contain a high proportion of positively charged arginine and lysine residues which are thought to interact with the cell membrane thereby initiating the uptake of the desired protein. Other mechanisms for protein delivery include microinjection and electroporation. Ideally an optimal protein transport reagent would be useful for a variety of proteins and target cells and would not exert significant toxicity on the target cell. A universal protein transport system using a native acellular bacterial product, like Invaplex, has not been described.

SUMMARY OF THE INVENTION

The present invention provides for the in vivo and in vitro use of Invaplex to transport materials, including functional proteins and biologically active nucleic acids, across eukaryotic cell membranes. The Invaplex can be in a composition form which would include the biologically active material, e.g. compound, of interest and the Invaplex in an amount sufficient to cause a eukaryotic cell to take up the compound. This composition can be placed in a kit wherein the composition is placed in a container. If desired, the Invaplex and the material of interest can be placed in separate containers in the kit. The kit can contain the materials in dosage amounts for a single application, if desired. The kit can contain additional reagents and instructions for use.

The invention also includes a process wherein the compound of interest and Invaplex are placed in close proximity to the eukaryotic cell membrane. The eukaryotic cell is contacted with the material and a sufficient amount of Invaplex to cause the cell to take up the material.

Invaplex is non-toxic to eukaryotic cells and induces endocytosis, which stimulates the uptake of nearby materials. Invaplex adheres to mammalian cell membranes and is internalized by mammalian cells. Invaplex does not cause cytopathic effects in vitro at concentration ranges of to 60 to 500 gg/ml. The eukaryotic cells can include a variety of cell types and sources, e.g. insect, reptile, fish, mammal and tumor cells.

The Invaplex complex is described in U.S. Pat. Nos. 6,277,379 and 6,245,892, the contents of which patents are expressly incorporated herein by reference.

In addition, Invaplex enhances the immune response to DNA vaccines and can function as a vaccine against shigellosis by itself.

Transported materials include biochemicals such as vectors (e.g., plasmids), reporter molecules, markers, antibiotics, antibodies, antigens, biopharmaceuticals, enzymes, receptors and hormones, carbohydrates including polysaccharides, lipopolysaccharides, polynucleotides, such as DNA and RNA, and glycoproteins, proteins, and peptides.

Intranasal delivery of DNA combined with Invaplex is a simple, noninvasive means for immunization that does not require swallowing or injection. Further the Invaplex delivery system does not require genetic manipulation, as would be required for live attenuated strains carrying vaccine DNA. The system is easily adapted to many different antigen systems. The formulation is a matter of mixing of the target DNA with Invaplex prior to immunization.

The invention has a variety of uses including but not limited to therapeutic uses including immunological based therapies, vaccines, gene therapy; research tool uses including genetic manipulation including changes in phenotypes and genotypes cell sorting; and manufacture of biologics including biopharmaceuticals and the like clinical and diagnostic.

BRIEF DESCRIPTION OF THE DRAWINGS

FIG. 1A shows untreated cells stained with Evan's Blue. FIG. 1B shows BHK-21 cells incubated overnight with *S. flexneri* 2a Invaplex-24 and stained with Evan's Blue. FIG. 1C shows BHK-21 cells incubated overnight with *S. flexneri* 2a Invaplex-50 and stained with Evan's Blue. FIG. 1D shows BKH-21 cells incubated overnight with GenePorter transfection reagent and stained with Evan's Blue.

DETAIL DESCRIPTION OF THE INVENTION

Figure 1A:
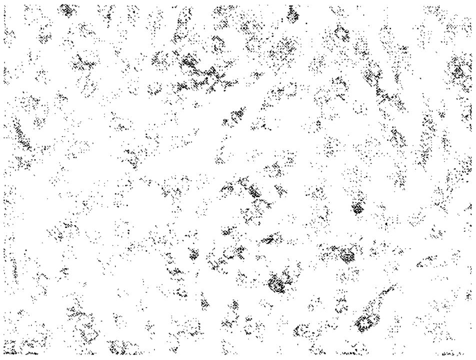
FIG. 1A-D show *S. flexneri* 2a Invaplex-Induced Cytotoxicity Assay.
Figure 1B:
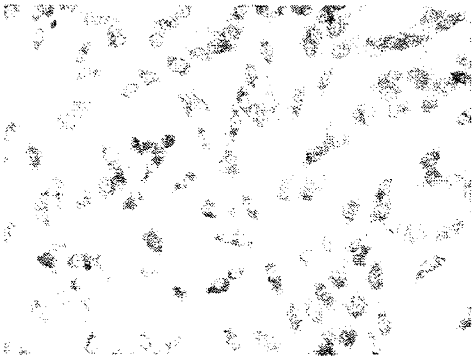
Figure 1C:
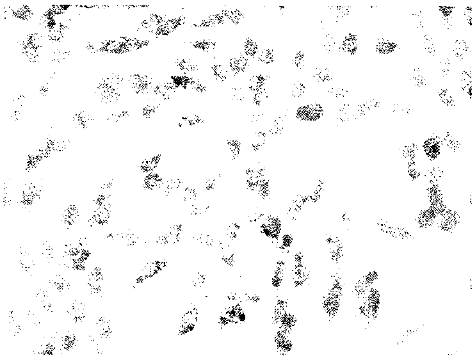
Figure 1D:
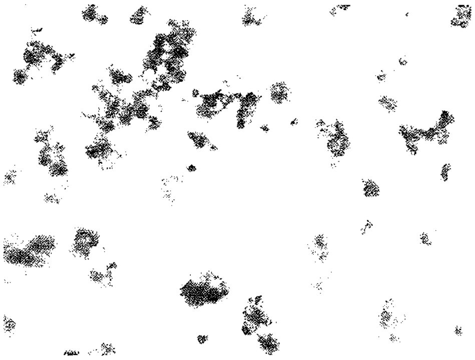

In vitro observations suggest that the Invaplex interacts with host-cell membranes eventually being translocated into the cytoplasm. This event is indicative of an induced endocytic event similar to the activity expressed by virulent shigellae. A hypothesis was that if a heterologous molecule (DNA or protein) is present at the time of Invaplex-induced endocytosis, the heterologous molecule would be taken up, non-specifically, by the host cell. Without the Invaplex stimulation such uptake would not occur. This has been demonstrated for Invaplex-induced uptake of naked DNA (expressing GFP, B-galactosidase or the Sta56 protein) or purified proteins (pure GFP, pure B-galactosidase or Sta56) by BHK cells, indicating that the Invaplex may be useful for delivering prophylactic or therapeutic molecules across eukaryotic cell membranes, thereby providing a safe and effective method for transfecting cells. The data below documents the interaction of Invaplex with host-cells, to Invaplex-induced uptake of DNA and proteins, and finally DNA immunization of mice using Invaplex to deliver the DNA.

EXAMPLES

Isolation and Characterization of Invaplex

Purification of *Shigella* Invasin Complex (Invaplex).

The *Shigella* Invaplex was isolated from water extracted proteins of virulent *Shigella* including *Shigella flexneri* 2a (2457T) and *S. sonnei* (Mosely). A modification of the original water extraction procedure (10) was used to prepare the material from which the *Shigella* invasin complex is isolated (20). Water extract batches positive for IpaB and IpaC were applied to an anion exchange FPLC (HiTrapQ, Pharmacia) column. Two peaks (measured at 280 ηm) containing the invasins and LPS were collected. The first peak (Invaplex 24) is eluted with 0.24M NaCl in 20 mM Tris HCl, pH 9.0 and the second peak (Invaplex 50) is eluted with 0.50 M NaCl in 20 mM Tris-HCl, pH 9.0. Each FPLC fraction was analyzed by immuno-spot blot using monoclonal antibodies (9) for the presence of IpaC and IpaB. Fractions containing the greatest amount of IpaB and IpaC in the Invaplex 24 peak were pooled as were peak Ipa protein fractions in the Invaplex 50 peak. The final pools were aliquoted and stored at −80° C.

*S. flexneri* 2a Invaplex-Induced Cytotoxicity Assay

BHK-21 cells (ATCC CCL-10), $5\times10^4$ cells per well in Minimum Essential Media (MEM) (Gibco, Rockville, Md.) supplemented with 1% L-glutamine (L-glut) (Gibco, Rockville, Md.) and 7% fetal calf serum (FCS) (Sigma, St. Louis, Mo.), were cultured overnight at 37° C., 5% $CO_2$ in a 96-well tissue culture plate (Costar, Acton, Mass.). *S. flexneri* 2a Invaplex 24 and Invaplex 50 (both from lot GNGO) were diluted with sterile, deionized water to isotonic levels (0.15M NaCl) and concentrated via Ultrafree-MC 30,000 MWCO centrifuge filters (Millipore, Bedford, Mass.). Final protein concentration was determined by bicinchoninic acid protein assay originally described by Smith et al (Pierce, Rockford, Ill.) (18). *S flexneri* 2a Invaplex 24 and 50 were then titrated, using MEM supplemented with 1% L-glut without FCS as the diluent in duplicate wells and incubated with the BHK-21 cells for 90 minutes at 37° C. Concentrations of Invaplex ranged from 500 μg/mL to 60 μg/mL.

A non-radioactive cytotoxicity assay (CytoTox 96® from Promega, Madison, Wis.) was used to determine release of lactate dehydrogenase (LDH), a stable cytosolic enzyme that is released from the cell's cytoplasm upon cell lysis or cell membrane damage. 10 μL of lysis buffer (9% v/v Triton X-100) was added at 90 minutes to non-Invaplex additional 30 minutes. The plate was centrifuged at 250×g for 5 minutes and 50 μL of supernatant from each well was transferred to a separate plate. 50 μL of LDH substrate, containing the tetrazolium salt INT (iodonitrotetrazolium chloride), was added to each well, covered from light and incubated at 37° C. for 30 minutes at which time 50 μL of stop solution (IM acetic acid) was added to each well and the absorbance was measured at 492 ηm. All samples were run in duplicate.

The percentage of cells exhibiting cytotoxic effects was calculated as the experimental LDH release (O.D. 490 ηm) divided by the maximum LDH release determined by the cells treated with lysis buffer (O.D. 490 ηm) multiplied by 100.

Adherence of *S. flexneri* 2a Invaplex 24 and 50 with Mammalian Cell Membranes

BHK-21 cells, diluted to $5\times10^3$ cells per well, were cultured in MEM supplemented with L-glut and 7% FCS overnight at 37° C., 5% $CO_2$, in 8-well, sterile, Lab Tek II Chamber Glass Slides with cover (Nalge Nunc International, Naperville, Ill.). Cells were washed 3 times with phosphate buffered saline (PBS) and incubated with either isotonic *S. flexneri* 2a Invaplex 24 (66.5 μg/well) or Invaplex 50 (27.7 μg/well) (both from lot GNGO) at 37° C., 5% $CO_2$. After 5, 10 and 30 minutes of incubation, two of the eight wells were selected and were washed 2 times with PBS and the cells fixed with 100% methanol. Negative control wells containing BHK-21 cells incubated with only cell culture media, were fixed at 30 minutes. All wells were then incubated at room temperature for 60 minutes with rabbit anti-*Shigella flexneri* 2a (strain 2457T) serum diluted 1:100 in PBS. Cells were then washed 3 times with PBS and incubated for 60 minutes at room temperature with Protein A-FITC diluted 1:1000 in PBS. Cells were washed 3× with PBS, once with deionized water, allowed to air dry, and viewed under a Nikon Optiphot 2 microscope using the EX470-490 excitation filter at 100× magnification.

Adherence of *S. sonnei* Invaplex 24 and 50 with Mammalian Cell Membranes

BHK-21 cells, diluted to $5\times10^3$ cells per well, were cultured in MEM supplemented with L-glut and 7% FCS overnight at 37° C., 5% $CO_2$ in 8 well chamber slides. Cells were washed 3 times with PBS and incubated with either isotonic *S. sonnei* (Mosley) Invaplex 24 or Invaplex 50 (50 μg/well lot FRFT and lot HKHL, respectively) at 37° C. At 5, 10 and 30 minutes of incubation, two of the eight wells were selected and the wells were washed 2× with PBS and cells fixed with 100% methanol. Negative control wells containing only BHK-21 cells incubated with media were fixed at 30 minutes.

All wells were then incubated at room temperature for 60 minutes with mouse polyclonal anti-*Shigella sonnei* serum diluted 1:100 in PBS. Cells were then washed 3× with PBS and incubated for 60 minutes at room temperature with goat-anti-mouse-TRITC (KPL, Gaithersburg, Md.) diluted 1:100 in PBS. Cells were washed 3× with PBS, 1× with deionized water, allowed to air dry and viewed under a Nikon Optiphot 2 microscope using the EX470-490 excitation filter at 20× magnification.

Transfection of Mammalian Cells with Plasmid DNA Encoding Green Fluorescent Protein (GFP) Using *Shigella* Invaplex as the Transfection Mediation Reagent.

BHK-21 cells, $5\times10^4$ cells per well, were cultured overnight at 37° C., 5% $CO_2$ in 8 well chamber slides. 0.5 μg of a plasmid (pEGFP-N1) (Gene Therapy Systems, San Diego Calif.) encoding GFP with a cytomegalovirus (CMV) promoter was incubated for 30 minutes at room temperature with either *S. flexneri* 2a Invaplex 24 or Invaplex 50 (both from lot GNGO) diluted to 10 μg/200 μL or 20 μg/200 μL in MEM and L-glut without FCS in a 1.5 ml eppendorf tube. As a positive control, the GFP plasmid was also incubated with GenePorter (Gene Therapy Systems, San Diego, Calif.) reagent as per manufacturer's directions. Negative controls included cell media only and plasmid pEGFP-N1 but no transfection reagent. After 30 minutes incubation, all wells were washed 3 times with MEM supplemented with L-glut. Cells were then treated with 200 μL of a mixture containing either the plasmid pEGFP-N1 and Invaplex 24 or Invaplex 50 (test samples); plasmid and GenePorter mixtures (positive control); plasmid pEGFP-N1 without a transfection reagent (negative control I); or with cell culture media alone in the appropriate slide chamber well. Cells were incubated for 3 hours, after which 100 μL of media containing 20% FCS was added to each well and cells incubated overnight at 37° C. Cells were then washed 3 times with PBS, fixed with methanol, and viewed under a Nikon Optiphot 2 microscope using EX470-490 excitation filter at 30× magnification.

The percent GFP positive cells was determined by first randomly choosing a field and counting the cells present using bright field microscopy. Fluorescent cells in the same field were then counted. The percentage cells positive for GFP expression was calculated by dividing the number of green fluorescent cells by the total number of cells in a particular field and multiplying by 100.

Transfection of Mammalian Cells with Plasmid DNA Encoding Beta-Galactosidase Using *Shigella* Invaplex as the Transfection Mediation Reagent.

BHK-21 cells, $5\times10^4$ cells per well, were cultured overnight at 37° C., 5% $CO_2$ in 8-well chamber slides. Plasmid DNA (0.5 μg) encoding beta-galactosidase (β-gal) linked to a CMV promoter (gWiz (β-galactosidase plasmid, Genetic Therapy Systems, San Diego Calif.) was incubated for 30 minutes at room temperature with either *S. flexneri* 2a Invaplex 24 or *S flexneri* 2a Invaplex 50 (lot GNGO) diluted to 10 μg/200 μL or 20 μg/200 μL in serum-free media. As a positive control the β-gal plasmid was also incubated with GenePorter (Gene Therapy Systems, San Diego Calif.) reagent as per manufacturer's directions. Negative controls included BHK cells with culture media only (no plasmid) and BHK cells with plasmid alone without a transfection reagent. After 30 minutes incubation, cells were washed 3× with serum-free media and 200 μL of the culture media, plasmid alone, plasmid-Invaplex, plasmid-GenePorter mixtures were added to the appropriate chamber. Cells were incubated for 3 hours, after which time, 100 μL of media containing 20% fetal calf serum (FCS) was added to each well and cells incubated overnight at 37° C. Cells were then washed 3× with PBS, fixed with methanol, and viewed by bright field microscopy.

The percentage of β-gal positive cells was determined by counting all of the cells present in a randomly chosen field using bright field microscopy. Blue cells in the same field were then counted. The percent β-gal positive was calculated by dividing the number of blue cells by the total number of cells and multiplying by 100.

Invaplex-Mediated Transport of Purified Recombinant GFP Protein Across Mammalian Cell Membranes BHK-21 cells, $5\times10^4$ cells per well, were cultured overnight at 37° C., 5% $CO^2$ in 8-well sterile glass Lab Tek II Chamber Slides with cover (Nalge Nunc International, Naperville, Ill.). Cells were washed 1× with serum-free media and incubated with GFP protein at 1 μg/well and either isotonic *S. flexneri* 2a Invaplex 24 (66, 33, or 15 μg/well) or isotonic *S. flexneri* 2a Invaplex 50 (28, 14, or 7 μg/well) (both from lot GNGO) at 37° C., 5% $CO^2$ overnight. Cell were washed 3× with PBS and fixed with 100% methanol, allowed to air dry and viewed under a Nikon Optiphot 2 microscope and EX470-490 excitation filter at 30× magnification.

The total number of cells were counted in a randomly chosen field of view in each well using bright-field microscopy and the number cells in the same field exhibiting green fluorescence was determined with a fluorescent microscopy. The percentage of GFP positive cells was determined by dividing the number of fluorescent cells by the total number of cells and multiplying by 100.

Invaplex-Mediated Transport of Beta-Galactosidase Protein Across Mammalian Cell Membranes BHK-21 cells, diluted to $5\times10^4$, were cultured overnight at 37° C., 5% $CO^2$ in 8 well chamber slides. Cells were washed 1× with serum-free media and incubated with β-gal protein at 10 units/well (Sigma, St. Louis, Mo.) and either *S. flexneri* 2a Invaplex 24 (66, 33, or 15 μg/well) or *S. flexneri* 2a Invaplex 50 (28, 14, or 7 μg/well), both isotonic (lot GNGO) at 37° C., 5% $CO^2$ overnight. Media was aspirated and cells washed 1× with PBS. 500 μL of fixing buffer from X-gal staining kit (Genetic Therapy Systems, San Diego, Calif.) was added to each well for 10 minutes at room temperature. Fixative was aspirated and cells washed 3× with PBS. 500 μL of freshly made X-gal staining buffer was added to each well and incubated for 90 minutes at 37° C. Cells were washed 3× with PBS (500 μL of PBS per well).

The total number of cells in a randomly chosen field of view were counted in each well using a light microscope and the number of those cells that were blue (β-gal positive) was determined. The percentage of β-gal positive cells was calculated by dividing the number of blue cells by the total number of cells and multiplying by 100.

Inhibition of Invaplex Adherence with *Shigella*-Specific Antibodies

BHK-21 cells, diluted to $5\times10^4$, were cultured overnight at 37° C., 5% $CO^2$ in 8 well chamber slides. Invaplex 24 (Lot GNGO, isotonic) was incubated at room temperature for 60 minutes with dilutions of antibodies specific for *Shigella* epitopes. Cells were washed 1× with serum-free media and incubated with each Invaplex/antibody combination at room temperature for 30 minutes. Cells were then washed 2× with PBS and fixed with 100% methanol. The fixed BHK cells were then incubated at room temperature for 60 minutes with rabbit anti-*S. flexneri* 2a (strain 2457T) serum (diluted 1:100 in PBS), washed 3× with PBS and finally incubated with Protein A-FITC diluted 1:1000 in PBS for 60 min. at room temperature. Cells were washed 3× with PBS, 1× with deionized water, allowed to air dry and viewed under a Nikon Optiphot 2 microscope and EX470-490 excitation filter at 20× magnification.

Inhibition of *Shigella* Invaplex Transfection Potential with *Shigella*-Specific Antibodies BHK-21 cells, diluted to $5\times10^4$, were cultured overnight at 37° C. in 8 well chamber slides. Plasmid DNA encoding GFP (Genetic Therapy Systems, San Diego, Calif.) was diluted in MEM supplemented with 1% L-glut to a final concentration of 2 μg/100 μL. *S. flexneri* Invaplex 50 and *S. flexneri* Invaplex 24 was diluted to 25 μg/100 μL in MEM supplemented with 1% L-glut. The diluted isotonic *Shigella* Invaplex was then mixed with equal volumes of the diluted plasmid DNA. Antibodies specific for *Shigella* IpaC, IpaB were added to the Invaplex-plasmid DNA mixtures at a final dilution of 1:100 and incubated at room temperature for 30 minutes. Media was aspirated from the BHK-21 culture slides and 200 μL of the Invaplex-plasmid DNA-antibody mixtures were added to the cells. Controls for the experiment included cells treated with plasmid DNA with and without *S. flexneri* Invaplex 24 or *S. flexneri* Invaplex 50 and cells treated with MEM supplemented with L-glut. Cells were incubated with the admixtures for 4 hours, 200 μL of MEM supplemented with 1% L-glut and 20% FCS was added to each well, and the cells were incubated for an additional 18 hours at 37° C. Cells were washed 3× with PBS and fixed with 100% methanol, allowed to air dry and viewed under a Nikon Optiphot 2 microscope and EX470-490 excitation filter at 30× magnification.

The total number of cells were counted in a randomly chosen field of view in each well using bright-field microscopy and the number cells in the same field exhibiting green fluorescence was determined with a fluorescent microscopy. The percentage of GFP positive cells was determined by dividing the number of fluorescent cells by the total number of cells and multiplying by 100.

Invaplex-Mediated Transport of *Orientia tsutsugamushi* 56k Protein and Plasmid DNA Encoding 56k Protein Across Mammalian Cell Membrane In Vitro BHK-21 cells, diluted to $5\times10^4$ cells per well, were incubated overnight in four-well glass chamber slides. Isotonic *S. flex* 2a Invaplex-50 and Invaplex-24 was diluted to 200 ug/mL in serum-free MEM supplemented with 1% L-glut. Plasmid DNA encoding the 56k protein was diluted to 500 ug/mL and purified 56k protein was diluted to 200 ug/ml and incubated with diluted Invaplex for 30 minutes at room temperature. Cells were washed two times with PBS and 300 uL of Invaplex-plasmid DNA or Invaplex-56k protein were added to wells 3 and 4 of the chamber slide. Equal amounts of plasmid DNA or purified 56k protein were added to well 2 while well 1 received only 300 uL of MEM supplemented with 1% L-glut. Slides containing Invaplex-protein preparations were incubated for 30 minutes at 37° C., washed 3 times with PBS, and fixed with 100% methanol. After a three hour incubation period at 37° C., 500 uL of MEM supplemented with 20% FCS and 1% L-glut was added to slides containing Invaplex-plasmid DNA preparations. These slides were then incubated overnight at 37° C., washed 3× with PBS, and fixed with 100% methanol. All chamber slide wells were then incubated at room temperature with 300 uL of mouse anti-56K ascites fluid (K13F88A; 11-5-87) diluted 1:100 in PBS, washed three times with PBS and subsequently incubated with goat anti-mouse IgG labeled with TRITC diluted 1:1000 in PBS. After three washes with PBS and one wash with deionized water, slides were air-dried and viewed under an Nikon Optiphot-2 microscope using an EX546/10 excitation filter at 100× magnification. Successful transport of 56K protein and transfection plasmid DNA encoding the 56K protein was determined by the presence of intracellular red fluorescence.

Invaplex-Mediated Delivery of Naked Plasmid DNA Encoding the *Orientia tsutsugamushi* 56K Protein for Intranasal Immunization of Mice.

Mice were immunized intranasally on weeks 0, 2, and 4 with plasmid DNA (100 or 2 ug) encoding the Rickettsial 56k protein formulated with or without 10 of *S. sonnei* Invaplex 50.[1] Two of the five animals per group were immunized on week 8 with r56k protein (5 ug) formulated with *S. sonnei* Invaplex 50 (5 ug). Plasmid DNA was provided by Dr. Wei-Mei Ching of NMRC.

Figure 15A:
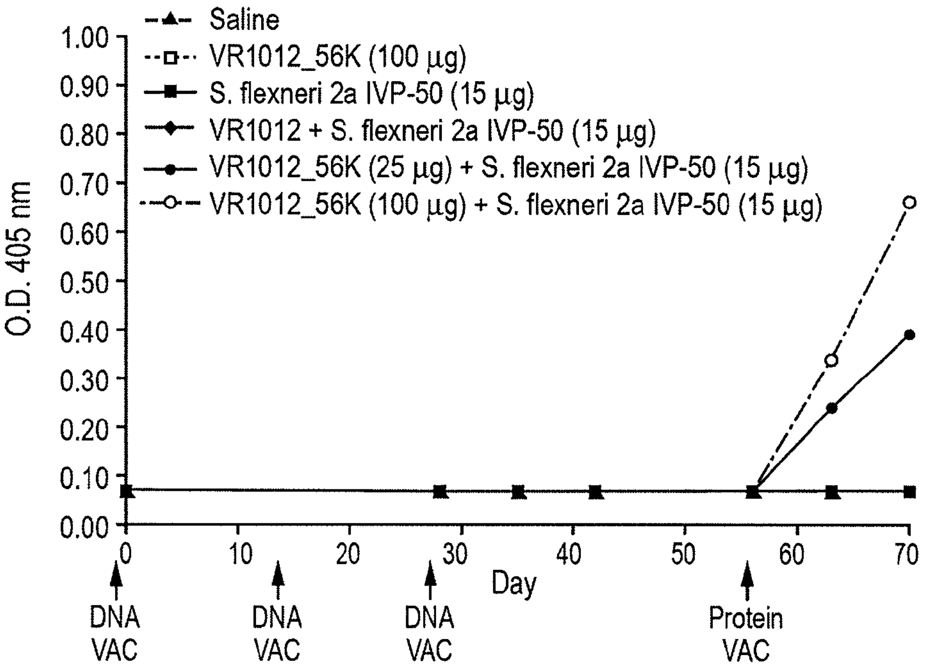
FIG. 15(A-B) show Anti-Sta56 and anti-*S. flexneri* 2a IVP-50 serum IgG responses in mice intranasally immunized with plasmid DNA encoding the sta56 gene from *O. tsutsugamushi* administered alone, or in combination with *S. flexneri* 2a IVP-50 and boosted with purified Sta56 protein combined with *S. flexneri* 2a IVP-50.
Figure 15B:
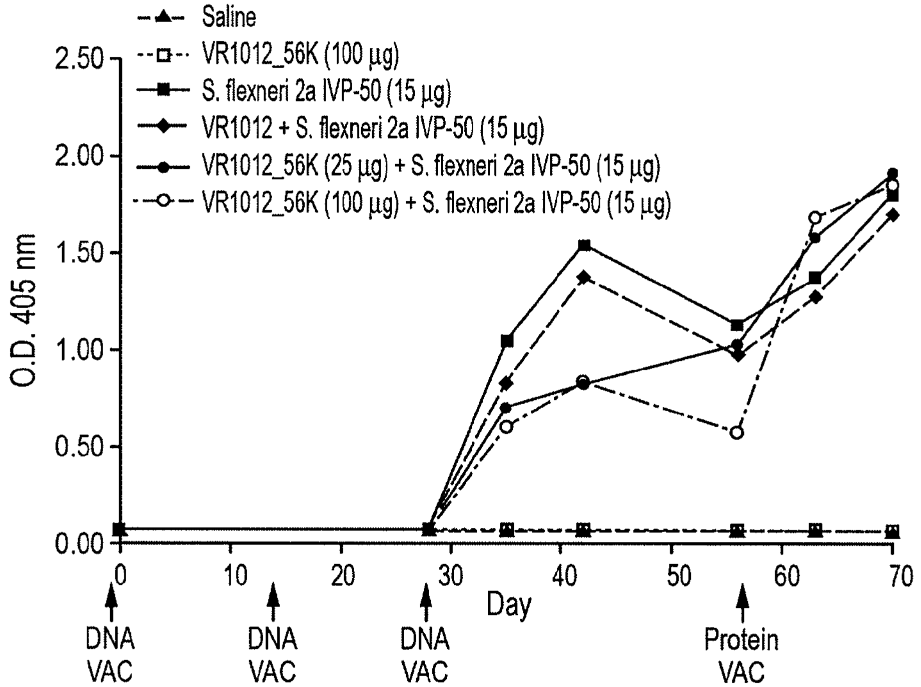

[1] Groups of mice were intranasally immunized on day 0, 14 and 28 with plasmid DNA encoding the sta56 gene from *O. tsutsugamushi* linked to a CMV promoter (pVR1012_56K) alone or pVR1012_56 K) (25 or 100 μg) combined with *S. flexneri* 2a IVP-50 (15 μg). Other groups of mice were immunized with saline, *S. flexneri* 2a IVP-50 (15 μg), or empty plasmid DNA vector (pVR 1012) combined with *S. flexneri* IVP-50 (15 μg). All groups were then intranasally immunized with recombinant Sta56 protein (15 μg) co-delivered with *S. flexneri* 2a IVP-50 (10 μg) on day 56. Blood was collected from all animals on days 0, 28, 35, 42, 56, 63, and 70. The Sta-specific (FIG. 15A) and *S. flexneri* IVP-50-specific (FIG. 15B) serum IgG responses were determined by ELISA. $OD_{405}$ values represent the mean $OD_{405}$ at a 1:180 (FIG. 15A) or 1:2880 (FIG. 15B) dilution of sample after a 60-minute incubation with substrate for each group of mice (n=5/grp).

Blood was collected at weeks 0, 4, 5, 9, 10, and 11 from each animal and cells from the spleen and cervical lymph nodes were collected from three of the five animals per group at week 6 upon sacrifice. Blood samples were assayed for anti-56k IgG responses using ELISA. Antigen-specific proliferative responses in cells from spleens and cervical lymph nodes were assessed using a colorimetric cell proliferation assay.

Detection of r56K Protein-Specific Serum Antibodies by ELISA

Detection of systemic antigen-specific antibodies was assessed by enzyme linked immunosorbant assay (ELISA). Recombinant 56k protein was diluted to 3 ug/mL in carbonate coating buffer (0.2 M carbonate, pH 9.8) and added to polysytrene 96-well antigen plates (0.3 ug/well) (Dynex Technologies, Inc. Chantilly, Va.). After overnight incubation at 4° C., plates were blocked for 30 minutes with casein (2% casein in Tris-saline buffer, pH 7.5). Serum samples were diluted in 2% casein, added to the antigen-coated plates, and incubated at room temperature for 2 hours. After four washes in phosphate-buffered saline (10.75 mM sodium phosphate, 145 mM NaCl, pH 7.4) with 0.05% Tween 20, plates were incubated with anti-mouse IgG conjugated with alkaline phosphatase (Kirkegaard & Perry, Gaithersburg, Md.). After incubation, plates were washed four times as above and the substrate, para-nitrophenyl phosphate (1 mg/ml in 10% diethanolamine buffer, pH 9.8 containing $M_gCl_2$ (0.1 mg/ml) and 0.02% sodium azide), was added to each well. Optical density was measured at 405 nm on a Molecular Devices (Menlo Park, Calif.) ELISA plate reader.

Antigen-Specific Lymphoproliferation Assays

Splenocytes were evaluated for antigen-specific lymphoproliferation by culturing lymphoid cells in complete media composed of RPMI 1640 supplemented with L-glutamine 4 mM, penicillin (100 U/ml), streptomycin (100 mg/ml), β-ME ($5\times10^{-5}$ M) and 10% heat-inactivated FCS. Proliferative responses to antigens and mitogens were measured by incubating $1\times10_5$ cells per well in 96-well U-bottom with either 5 or 1 μg of r56k, or *S. flexneri* 2a Invaplex 50. A subset of the cells were stimulated with concanavalin A as a positive control. Negative controls included immune cells incubated with complete medium alone and cells from naive mice stimulated with antigen. Assays were performed in triplicate and plates were incubated at 37° C. in 5% $CO_2$.

Lymphoproliferation was assessed after 3-5 days of culture using a non-radioactive cell proliferation assay (CellTiter 96® Aqueous Assay, Promega) as per the manufacturer's directions. Briefly, plates were centrifuged at 250×g for 5 minutes and 100 uL of cell supernatant was transferred to a new flat bottom, 96-well microtiter plates and stored at −70° C. until assayed for cytokine concentrations. 20 μL, of the MTS-PMS reagent was added to the remaining 100 uL of supernatant and the plates were incubated at 37° C. for 1-4 hours. Absorbance at 492 nm was measured after adding 25 μL of 10% SDS to stop the reaction.

Stimulation indices were calculated by dividing the mean optical density recorded in wells with antigen-stimulated cells by mean optical density recorded in wells with medium-only stimulated cells (19). The stimulation index (SI) of cells from mice immunized with adjuvant and antigen were compared to the SI of cells from non-immunized mice, and mice immunized with antigen alone or adjuvant alone.

Results Section

Invaplex-Induced Cytotoxicity Assay

Neither Invaplex 24 nor Invaplex 50 displayed measurable cytotoxic effects as determined by LDH release in the concentration range of 6 to 50 μg/100 μL. Background levels of cytotoxicity as determined with media only controls were also observed with Invaplex treated cells. In contrast cells treated with GenePorter exhibited a much higher level of cytotoxicity as determined by LDH release. (See Table 1.)

This data is consistent with microscopy observations made during this and other assays in which no detectable morphological changes appear in BHK-21 cells incubated with Invaplex for extended periods of time ranging from 4 to 24 hours (FIG. 1A-D). In contrast, cells incubated with GenePorter transfection reagent underwent significant morphological changes often resulting in lower proportion of viable cells.

TABLE 1

Percent Cytotoxicity of Invaplex-Treated Cells

| Sample | Amount (μ) | % Cytotoxicity |
|---|---|---|
| Lysis buffer (9% Triton-X) | 10 μL | 100.00 |
| Media Only | N/A | 5.99 |
| GenePorter | 1:4 dilution | 31.3 |
| GenePorter | 1:8 dilution | 16.0 |
| *S. flexneri* 2a Invaplex 24 | 50 | 4.27 |
| *S. flexneri* 2a Invaplex 24 | 25 | 6.16 |
| *S. flexneri* 2a Invaplex 24 | 12.5 | 6.16 |
| *S. flexneri* 2a Invaplex 24 | 6 | 7.27 |
| *S. flexneri* 2a Invaplex 50 | 50 | 4.27 |
| *S. flexneri* 2a Invaplex 50 | 25 | 6.59 |
| *S. flexneri* 2a Invaplex 50 | 12.5 | 6.78 |
| *S. flexneri* 2a Invaplex 50 | 6 | 5.85 |

Adherence of *S. flexneri* 2a *Shigella* Invaplex with Mammalian Cell Membranes

Figure 2A:
FIGS. 2A and B show, respectively, the adherence of mammalian cell membranes with *S. flexneri* 2a Invaplex 24 (FIG. 2A) or with Invaplex 50 (FIG. 2B).
Figure 2B:
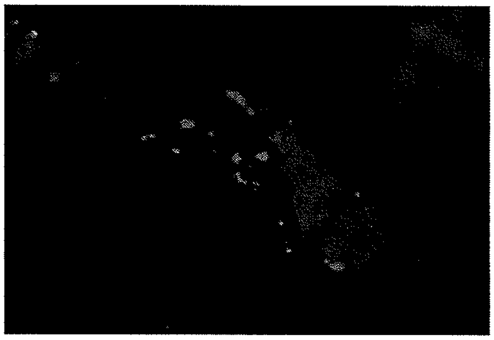
FIG. 2C shows the internalization of Invaplex within the cell.
Figure 2C:
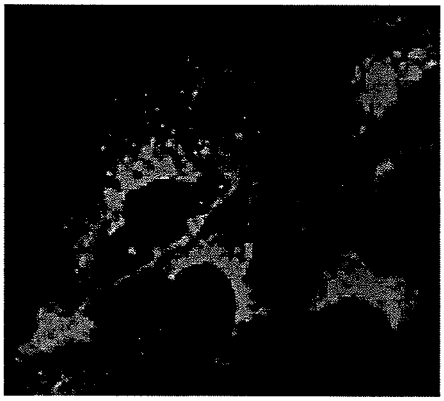

BKH-21 cells were incubated with Invaplex 24 (FIG. 2*a*) or with Invaplex 50 (FIG. 2*b*) for 5 minutes at 37° C. or with Invaplex 24 for 30 minutes (FIG. 2*c*). Cells were then incubated with rabbit anti-*S flexneri* serum, washed, and subsequently incubated with Protein A conjugates with FITC. Invaplex location determined by recording green fluorescence with Nikon Optiphot 2 and EX470-490 excitation filter at 60× magnification.

No observable fluorescence was noted in media only and Invaplex-free controls indicating that the fluorescence observed in each well was Invaplex-associated. The level of fluorescence was similar for Invaplex 24 and Invaplex 50 preparations despite the fact that approximately 50% less Invaplex 50 was used as compared to the Invaplex 24 in these experiments.

Invaplex-Specific Staining Pattern on the Host Cell Surface

Small fluorescent patches were noted after a 5-minute incubation as bright, semi-round decorations or patches localized at several positions along the cell periphery or surface of the BHK-21 cells (FIGS. 2A and 2B). The antigen deposition appeared to be distributed randomly on the cell surface. After 10 minutes, the amount of extracellular fluorescence was diminished by approximately 40% resulting in fewer areas of antigen deposition. A further reduction in surface-localized fluorescence was observed at 30 minutes.

Intracellular Invaplex-Specific Staining Pattern

In general, intracellular fluorescence increased with time of incubation and was specific to those cells that also exhibited extracellular fluorescent particles. After a 30-minute incubation, the green fluorescence localized to areas surrounding the cell nucleus in a more diffuse manner (FIG. 2C) when compared to the extracellular fluorescence which was isolated in bright fluorescent patches.

TABLE 2

Intracellular and Extracellular Antigen Localization of *S flexneri* 2a Invaplex Treated BRK cells

| Sample | 5 min. Observations | 10 min. Observations | 30 min. Observations |
|---|---|---|---|
| Media Only | No observable fluorescence (intra/extracellular) | No observable fluorescence (intra/extracellular) | No observable fluorescence (intra/extracellular) |
| ProA-FITC + Rabbit Serum (Invaplex free) | No observable fluorescence | No observable fluorescence | No observable fluorescence |
| Invaplex 24 (66.5 ug/well) Invaplex 50 (27.7 ug/well) | Extracellular: >60% of cells had distinct, small fluorescence patches at cell periphery decorating cellular membranes. The average number of patches per cell was 2 to 4. | Extracellular: 40-60% of cells had distinct fluorescent particles lining (peppering) cell membranes. The average number of particles per cell was 1 to 2. | Extracellular: 30-40% of cells had distinct fluorescent particles lining (peppering) cell membranes. The average number of particles per cell was 1 to 2. |
| Invaplex 24 (66.5 ug/well) Invaplex 50 (27.7 ug/well) | Intracellular: <10% of cells have Low-level intracellular fluorescence. Only cells with particles on | Intracellular: >30% of cells have low-level intracellular fluorescence. Only cells with particles on | Intracellular: >50% of cells have low-level intracellular fluorescence. Only cells with particles on |

TABLE 2-continued

| Intracellular and Extracellular Antigen Localization of *S flexneri* 2a Invaplex Treated BRK cells | | | |
|---|---|---|---|
| Sample | 5 min. Observations | 10 min. Observations | 30 min. Observations |
| | their surfaces exhibited intracellular fluorescence. | their surfaces exhibited interior fluorescence. | their surfaces exhibited interior fluorescence. |

Adherence of *S. sonnei* Invaplex 24 and 50 with Mammalian Cell Membranes

Figure 4A:
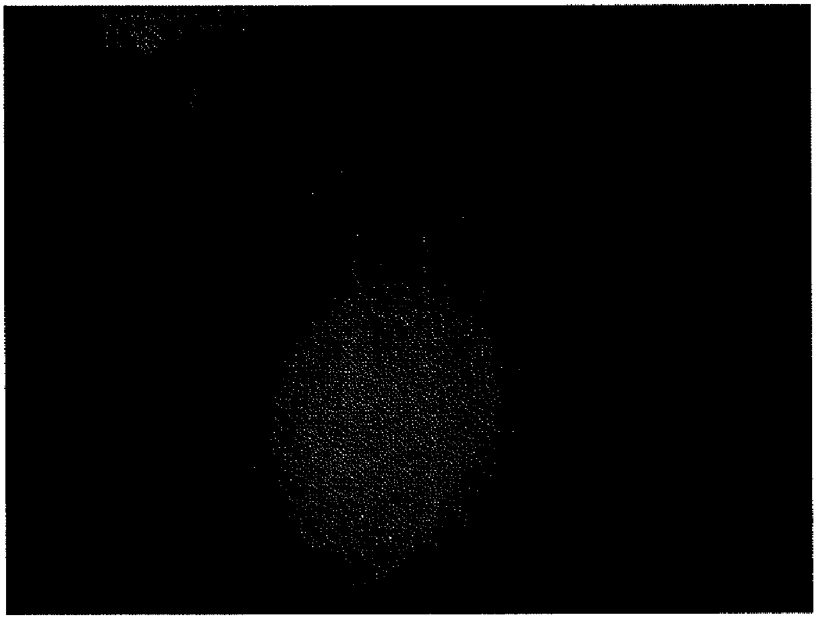
FIG. 4(A, B) show Invaplex *S. sonnei* 24 interacting with BHK-21 fibroblast cell.
Figure 4B:
Figure 5:
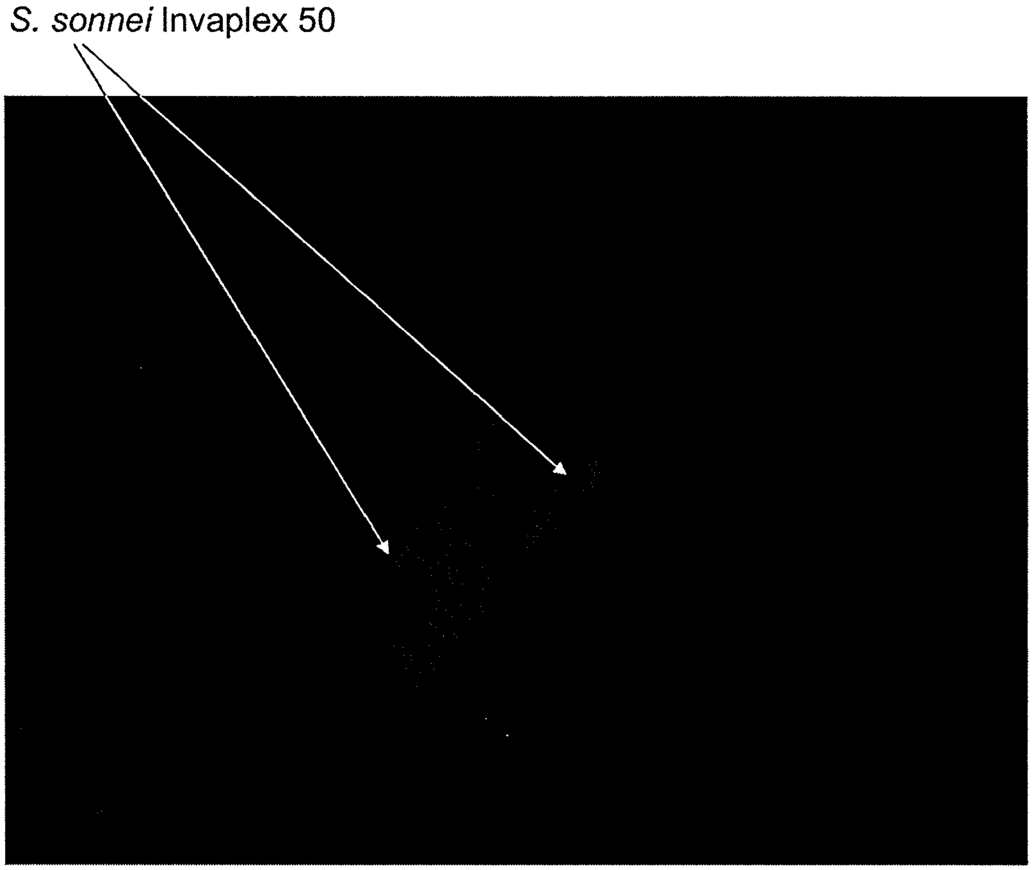
FIG. 5 shows Invaplex *S. sonnei* 50 interacting with BHK-21 fibroblast cell.
Figure 6A:
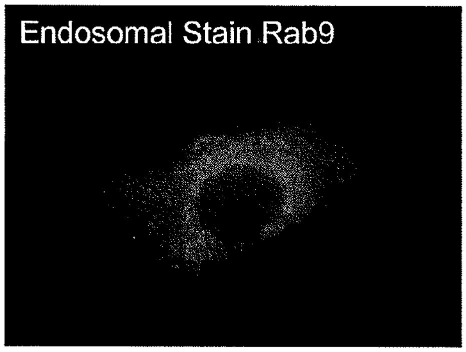
FIG. 6(A-F) show *S. flexneri* Invaplex-24 located within early and late endosomes.
Figure 6B:
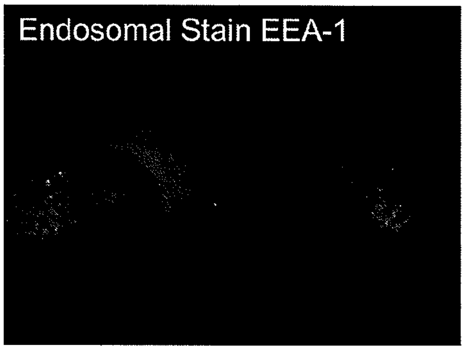
Figure 6C:
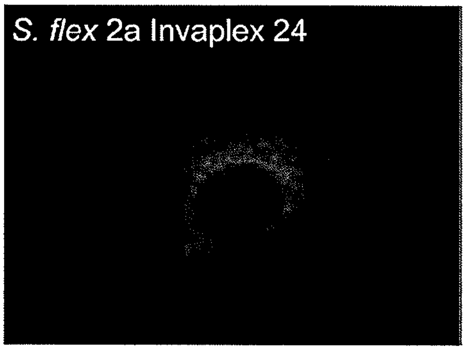
Figure 6D:
Figure 6E:
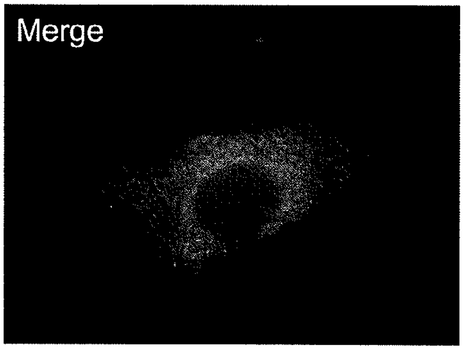
Figure 6F:
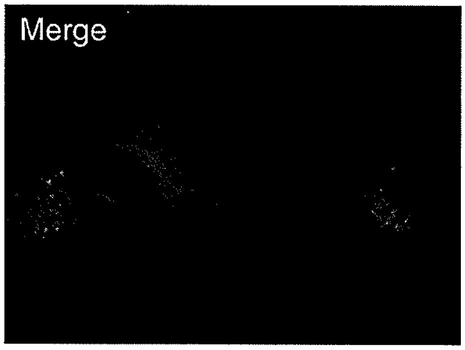

Similarly to Invaplex 24 and 50 from *S. flexneri* 2a, Invaplex from *Shigella sonnei* adheres to BHK-21 cells and is internalized after 5 to 30 minutes. Invaplex can be found throughout the cytoplasm of the cell, with a strong presence near the nuclear membrane. (FIG. 3(A-F), FIG. 4(A, B), and FIG. 5)

Figure 3A:
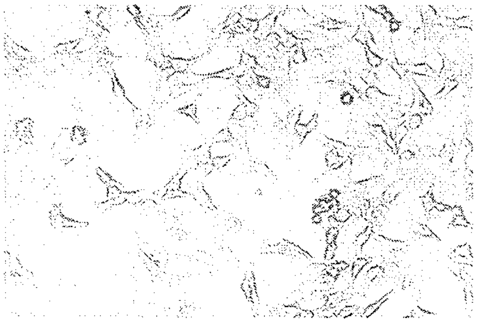
FIG. 3(A-F) show *S. sonnei* Invaplex 24 and 50 adherence to BHK-21 fibroblast cells.
Figure 3B:
Figure 3C:
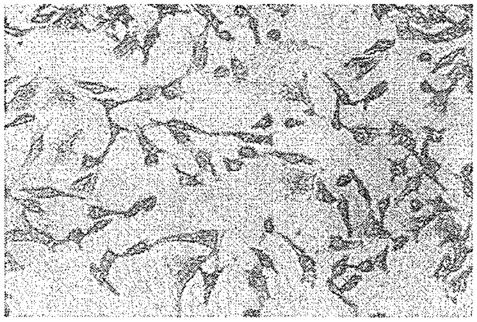
Figure 3D:
Figure 3E:
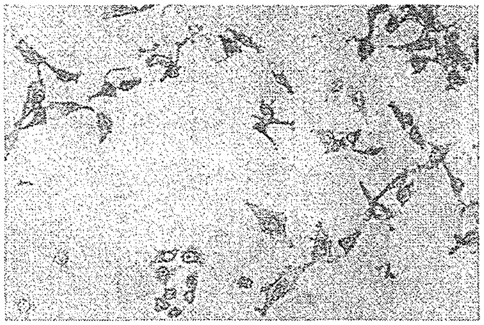
Figure 3F:

FIGS. 3A, 3C, and 3E are BHK-21 cells viewed under a bright field microscope (Nikon Optiphot 2) at 20× magnification. The same field is then shown in FIGS. 3B, 3D, and 3F (Nikon Optiphot 2 and EX470-490 excitation filter at 20× magnification. Cells in FIGS. 3A and 3B were incubated with MEM supplemental with 1% L-glut and 7% FCS alone, cells in FIGS. 3C and 3D were treated with *S. sonnei* Invaplex 24, and cells in FIGS. 3E and 3F with *S. sonnei* Invaplex 50. Bound Invaplex was detected with anti-mouse *S. sonnei* followed by a rhodamine labeled ant-mouse IgG. (Data taken from experiment dated 26 Sep. 2002 in lab notebook titled "In vitro Invaplex Experiments—Volume I, 22 Mar. 2001 to Present")

BHK-21 fibroblast cells alone (FIG. 4A) or incubated with *S. sonnei* Invaplex 24 (FIG. 4B) for 5 minutes, fixed with acetone, washed and incubated with mouse anti-*Shigella sonnei* antibodies which were detected using anti-mouse-TRITC. Actin is stained with phalloidin-FITC and the nucleus with propidium iodide.

BHK-21 fibroblasts were treated with *S. sonei* Invaplex 50 for 10 minutes, fixed with methanol, and incubated with anti-*Shigella sonnei* antibodies raised in mice. After washing thoroughly, wells were incubated with anti-mouse antibodies conjugated to FTTC. Cells were counter stained with Evan's Blue. *S. sonnei* Invaplex 50 can be seen on the cell's periphery and in the cytoplasm. See FIG. 5.

Intracellular Co-Localization Experiments

To study the interactions between mammalian host cell organelles and *Shigella* Invaplex, BHK-21 fibroblast or HeLa epithelial cells were incubated with Invaplex for various times, were fixed for 10 minutes with 10% formalin and permeabilized with 0.1% saponin.[2] Cells were then probed with antibodies specific for Invaplex and intracellular organelles or vesicles, to include early endosomes (rabbit anti-Early Endosomal Antigen (EEA-1); Affinity BioReagents) (28), late endosomes (rabbit anti-Rab 9; Affinity BioReagents) (29, 30), and the Golgi apparatus (mouse anti-58k protein, Sigma) (31, 32). After extensive washes with 0.1% saponin in PBS, the cells were incubated with secondary antibodies (Goat anti-Mouse or anti-Rabbit-IgG labeled with either Oregon Green or Texas Red; Molecular Probes). The washed cells were then examined at 60× magnification with a Nikon Optiphot-2 microscope equipped with green, and red bandpass emission/excitation filter sets.

[2] BHK-21 fibroblasts were incubated overnight at 37° C. in 8 well glass chamber slides, washed twice with PBS, and incubated with *S. flexneri* Invaplex-24 for 15 minutes at 37° C. Cells were then washed three times with PBS and fixed for 10 minutes with 10% formalin. Fixed cells were probed with polyclonal mouse antibodies specific for *Shigella* Invaplex antigens and polyclonal rabbit antibodies specific for early endosomes (EEA-1) and late endosomes (Rab9). Bound antibodies were subsequently detected with GAM-IgG-TRITC (KPL) or GAR-IgG-FITC (KPL). The cells were examined at 60× magnification with Nikon Optiphot-2 microscope equipped with green, and red bandpass emission/excitation filter sets. Images were captured with a Pixera 600CL cooled CCD camera and processed for publication in Photoschop 7.

Results from these studies indicate that Invaplex co-localized with various host cell organelles depending on the duration of incubation. Invaplex is first found in early endosomes and appears as punctuated areas of activity in the cytoplasm. Later the activity "migrates" towards the nucleus and co-localizes with late endosomes (see table 3 and FIG. 6A-F). Next the Invaplex activity co-localizes with the Golgi apparatus in a perinuclear staining pattern. Finally, the pattern of Invaplex staining appears diffusely in the cytoplasm indicating release from either the late endosomes or the Golgi.

TABLE 3

| Time points of Invaplex-Intracellular Organelle Marker Co-localization | | | | |
|---|---|---|---|---|
| Time point | Early Endosomal Markers | Late Endosomal Markers | Golgi apparatus Markers | Invaplex free in Cytoplasm |
| 1 min | + | | | |
| 5 min | + | + | | |
| 15 min | + | + | | |
| 30 min | | + | + | |
| 60 min | | | + | + |

The data in the above table was compiled from multiple experiments investigating the intracellular localization of Invaplex after various incubation times with mammalian host cells. Each series of experiments focused on individual intracellular organelle markers co-localizing with Invaplex at specific incubation times.

Possible Implications of Intracellular Invaplex

There are several possible outcomes of Invaplex-mediated uptake into host cells, dependent on the cell type. Invaplex-mediated uptake into non-polarized epithelial cells such as those used in the experiments presented in Table 3 could result in the presentation of Invaplex antigens in the context of MHC class I molecules. This would be important to the adjuvanticity of Invaplex.

Invaplex-mediated uptake into polarized epithelial cells could result in presentation of Invaplex-antigens to the underlying lymphoid cells via MHC class I pathway. Alternatively, transport of Invaplex from the apical to the basolateral surface could be accomplished through the sorting mechanism of apically and basolaterally-derived endosomes.

Invaplex-mediated uptake into antigen presenting cells of the immune system could result in the presentation of Invaplex, and co-delivered antigens, via the MHC class I or MHC class II pathway, depending on whether Invaplex and the antigens escape from the endosomal vacuoles.

Figure 7A:
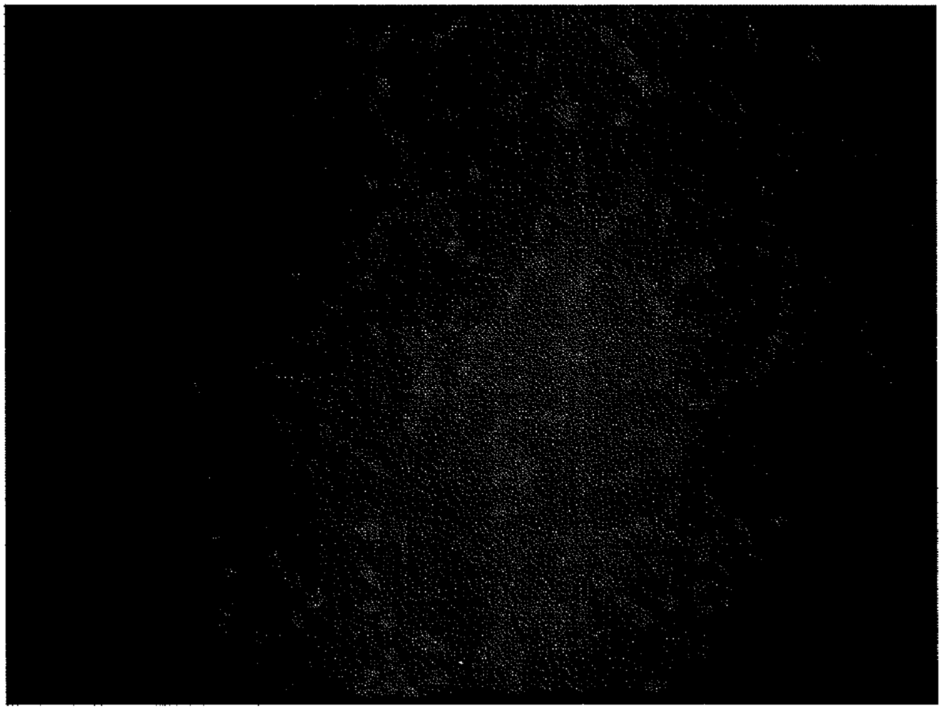
FIG. 7(A, B) show *S. flexneri* 2a Invaplex-mediated GFP plasmid transfection.
Figure 7B:
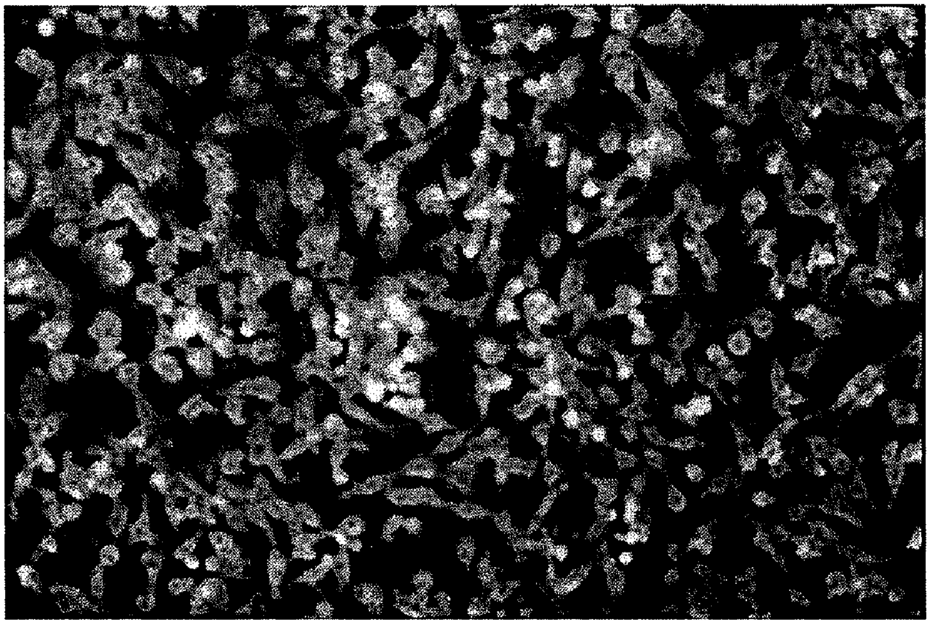

Use of Invaplex to Mediate Transfection of Mammalian Cells with Plasmid DNA Encoding the Green Fluorescent Protein Both *S. flexneri* 2a Invaplex 24 and Invaplex 50 were capable of stimulating uptake of plasmid DNA. The level of DNA uptake and subsequent expression was greater in cells incubated with a higher concentration (20 μg) of Invaplex as compared to 10 μg of Invaplex. The level of plasmid DNA uptake was determined by the relative amounts of fluorescence in the cells. See FIG. 7(A, B).[3]

[3] BHK-21 cells were incubated with plasmid DNA (Gene Therapy Systems, San Diego, Calif.) with the green fluorescent protein (GFP) gene linked to a CMV promoter (FIG. 7A) or GFP-plasmid DNA and Invaplex 24 (FIG. 7B) or plasmid DNA and Invaplex 50 (data not shown) overnight at 37° C. GFP expression was determined by the amount of green fluorescence localized in the cytoplasm of the transfected cells. The image was recorded with a Nikon Optiphot 2 and EX470-490 excitation filter at 20× magnification.

Cells incubated with GenePorter/plasmid DNA mixtures showed the highest level of GFP expression. However, BHK cells treated with the GenePorter Transfection reagent were rounded and not fully extended indicating a level of cytotoxicity whereas the Invaplex treated cells where morphologically indistinguishable from the non-treated cells.

TABLE 4

Relative Amount of Green Fluorescence in BHK cells Transfected with plasmid DNA encoding GFP

| | No Transfection Reagent | Invaplex 24 (10ug) | Invaplex 24 (20 ug) | Invaplex 50 (10 ug) | Invaplex 50 (20 ug) | GenePorter |
|---|---|---|---|---|---|---|
| GFP Plasmid | − | ++ | +++ | ++ | +++ | +++++ |
| No GFP Plasmid | − | − | − | − | − | − |

Invaplex-Mediated Transfection of Mammalian Cells with Plasmid DNA Encoding β-gal.

BHK-21 cells were efficiently transfected with plasmid DNA, encoding the β-galactosidase gene under the control of a CMV promoter, when incubated with a mixture of plasmid DNA and Invaplex 24 or Invaplex 50.[4] Similar to the previous section, uptake of plasmid DNA was greater with a higher concentration of Invaplex (20 μg) as compared to transfection with 10 μg of Invaplex. The level of transfection was determined by counting the number of cells expressing β-galactosidase. See FIG. 8(A-C).

[4] BHK-21 cells were incubated with β-gal protein (FIG. 8A) or β-gal protein and Invaplex 24 (FIG. 8B) or β-gal protein and Invaplex 50 (FIG. 8C) overnight at 37° C. B-gal protein activity was determined colormetrically through the addition of X-gal substrate (Gene Therapy Systems, San Diego, Calif.). Cells expressing β-gal activity have a blue cytoplasm.

There was significantly less cytopathic effect when Invaplex was used as a transfection reagent as compared with GenePorter. In the presence of Invaplex, cells remained adherent and morphologically indistinguishable from non cells.

TABLE 5

Relative Amount of β-galactosidase activity (blue color) in BHK cells Transfected with DNA Plasmid encoding β-galactosidase

| | No Transfection Reagent | Invaplex 24 (10 ug) | Invaplex 24 (20 ug) | Invaplex 50 (10 ug | Invaplex 50 (20 ug) | GenePorter |
|---|---|---|---|---|---|---|
| β-gal plasmid | − | + | +++ | + | +++ | ++++ |
| No β-gal plasmid | − | − | − | − | − | − |

Invaplex-Mediated Transport of Purified Green Fluorescent Protein (GFP) Across Mammalian Cell Membranes The highest percentage of GFP positive cells was found to be in wells with the lowest amount of Invaplex (Table 9). Fluorescent activity was low in all of the positive cells indicating transport of active GFP. The level of GFP activity was higher in cells transfected with GFP plasmid as compared to cells treated with Invaplex-GFP protein mixtures which is likely due to continued expression of the gfp gene once inside the cell, resulting in a higher amount of GFP protein in the cell. Also of interest was the apparent loss of cells in wells incubated with higher concentrations of Invaplex in combination with GFP. This may be due to an unknown toxicity of the GFP on mammalian cells or due to an effect of Invaplex on the adherence mechanism of BHK cells. See FIG. 9(A-F).[5]

TABLE 6

Percentage of GFP-Positive BHK cells Treated with GFP protein and Invaplex.

| | Media | GFP | Invaplex 24 | | | Invaplex 50 | | |
|---|---|---|---|---|---|---|---|---|
| | Only | Only | 66 μg | 33 μg | 15 μg | 28 μg | 14 μg | 7 μg |
| Amount of Adherent Cells | +++++ | +++++ | ++ | +++ | ++++ | ++ | +++ | ++++ |
| Percent GFP+ Cells | 0% | 2% | 17% | 34% | 47% | 12% | 43% | 57% |

Invaplex-Mediated Transport of β-gal Protein Across Mammalian Cell Membrane

Figure 10A:
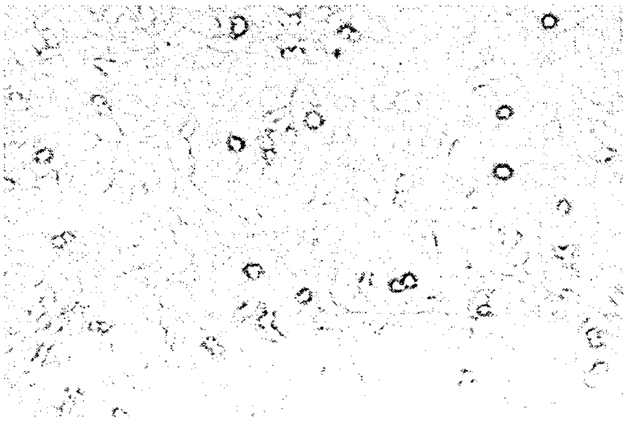
FIG. 10(A-C) show Invaplex-Mediated Transport of beta-Galactosidase protein across mammalian cell membrane.
Figure 10B:
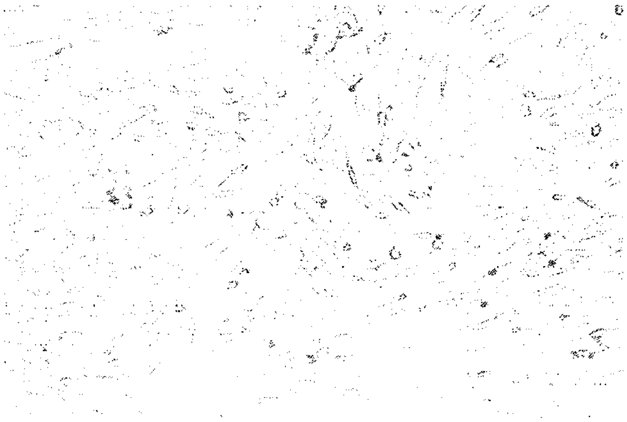
Figure 10C:
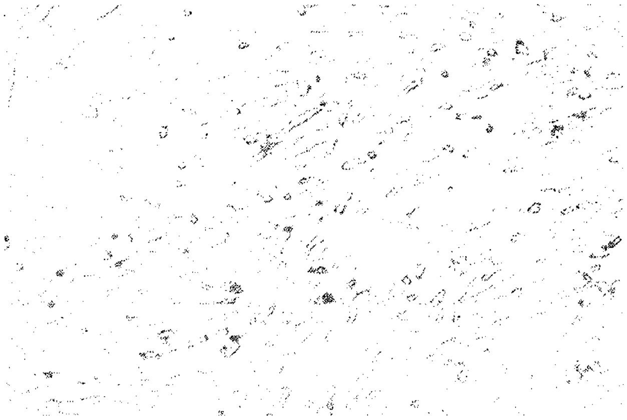

There was an inverted trend in the amount of adherent cells in a well and the amount of Invaplex-B-gal mixture incubated with those cells. In general, higher amounts of the Invaplex B-gal mixture resulted in lower amounts of adherent cells at 24 hours (Table 8). This could be the result of an excess of β-gal being imported into the cell resulting in toxicity or an effect of Invaplex on the adherence mechanism of BHK cells. See FIG. 10(A).

Figure 8A:
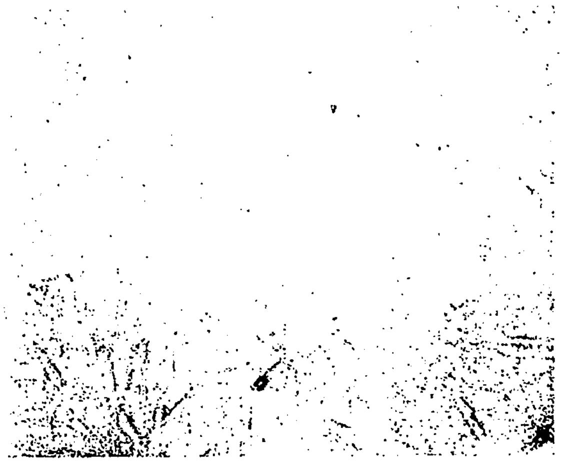
FIG. 8(A-C) show *S. flexneri* 2a Invaplex-Mediated beta-Galactosidase plasmid transfection.
Figure 8B:
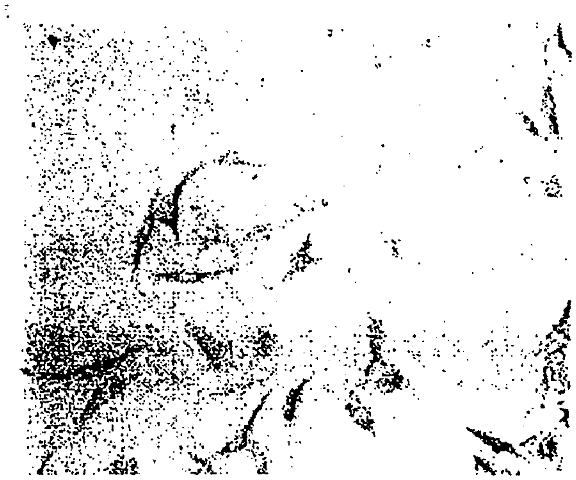
Figure 8C:
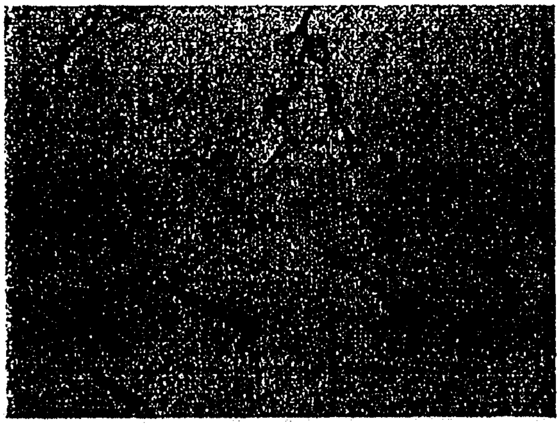
Figure 9A:
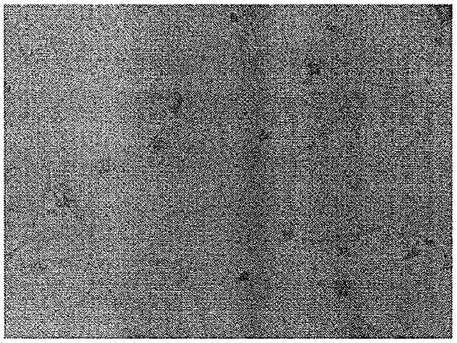
FIG. 9(A-F) show Invaplex-Mediated Transport of Green Fluorescent Protein across mammalian cell membrane.
Figure 9B:
Figure 9C:
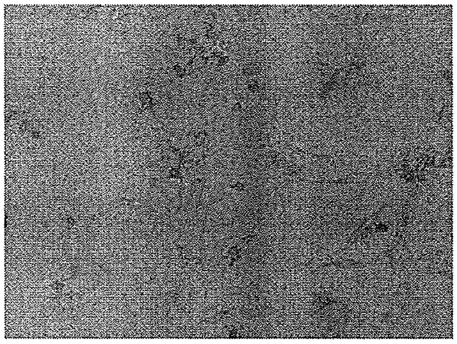
Figure 9D:
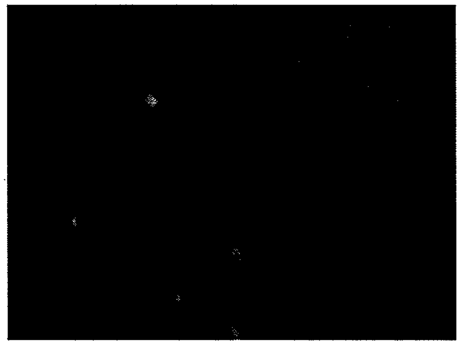
Figure 9E:
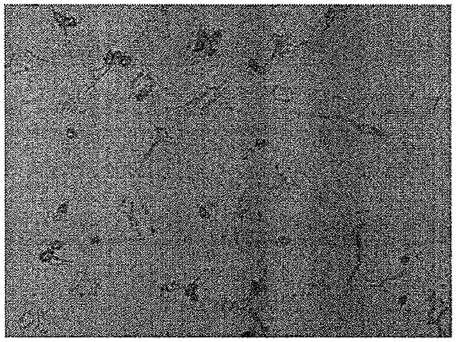
Figure 9F:

FIG. 8A shows plasmid DNA encoding the β-gal protein incubated with BHK-21 cells (negative control). FIG. 8B shows plasmid DNA encoding the β-gal protein and *S. flexneri* 2a Invaplex 24 incubated with BHK-21 cells (Most of the cells have a light blue color in the cytoplasm indicating beta-galactosidase expression). FIG. 8C shows plasmid DNA encoding the β-gal protein and *S. flexneri* 2a Invaplex-50 incubated with BHK-21 cells (The cells with a light blue color in the cytoplasm indicate beta-galactosidase expression).

TABLE 7

Percentage of β-gal Positive Invaplex-Treated BHK cells

| | Media | GFP | Invaplex 24 | | | Invaplex 50 | | |
|---|---|---|---|---|---|---|---|---|
| | Only | Only | 66 μg | 33 μg | 15 μg | 28 μg | 14 μg | 7 μg |
| Amount of Adherent Cells | +++++ | +++++ | + | ++ | ++++ | + | ++ | ++++ |
| Percent GFP+ Cells | 0% | 0.1% | 10% | 28% | 34% | 8% | 22% | 46% |

Inhibition of Invaplex Adherence to BHK Cells with *Shigella* Antibodies

Invaplex adherence to mammalian cell membranes was inhibited by polyclonal serum raised against whole *Shigella* and by polyclonal serum reactive with IpaC. Polyclonal antibodies reactive with only IpaB or serum from naive animals did not significantly inhibit the adherence of Invaplex to mammalian cell membranes. These data suggest that the ability of Invaplex to bind to host cell membranes may require interactions between IpaC and host cell surface structures.

TABLE 8

Inhibition of *S. flexneri* 2a IVP-24 internalization into BHK-21 cells with polyclonal mouse sera or monoclonal antibodies specific for *Shigella flexneri* 2a antigens

| *S. flexneri* 2a IVP-24 (μg/ml) | Blocking Antibody Specificity | Percent Cells Invaplex-Positive[a] | % Inhibition (Enhancement)[b] |
|---|---|---|---|
| 0 | N/A | 0% | 0.0% |
| 0 | *S. flexneri* 2a IVP-24 | 0% | 0.0% |
| 100 | N/A | 56.6% | 0.0% |
| 100 | Non (Pre-Bleed) | 53.8% | 4.6% |
| 100 | *S. flexneri* 2a IVP-24 | 5.7% | 90.6% |
| 100 | *S. flexneri* 2a IVP-24 | 10.7% | 83.1% |
| 100 | *S. flexneri* 2a IVP-50 | 11.4% | 82.6% |
| 100 | *S. flexneri* 2a IVP-50 | 17.7% | 72.8% |
| 100 | IpaB | 33.3% | 40.6% |
| 100 | IpaC | 4.8% | 91.5% |
| 100 | *S. flexneri* 2a LPS | 58.1% | (2.4%) |

The ability of polyclonal mouse sera, with specificity for *S. flexneri* 2a IVP-24 and IVP-50 antigens, and monoclonal antibodies specific for IpaB, IpaC, or LPS to inhibit the internalization of *Shigella* Invaplex was investigated by incubating serum from immunized mice or monoclonal antibodies with *S. flexneri* 2a IVP24. The antibody-Invaplex mixtures were then incubated at 37° C. for 30 minutes in duplicate with separate BHK-21 fibroblast monolayers. Controls for the assay included monolayers treated with mouse antibody in the absence of Invaplex (negative control) and monolayers treated with Invaplex in the absence of antibody (positive control). After incubation, the monolayers were washed with PBS to remove noncell-associated Invaplex and fixed with formalin. The internalization of *Shigella* Invaplex into BHK-21 cells was detected by probing the formalin-fixed cells with polyclonal rabbit sera specific for *Shigella* Invaplex antigens (Rabbit 7) for 2 hours at RT. The monolayers were washed and bound anti-Invaplex mouse antibodies were detected with fluorescently-labeled anti-rabbit IgG. Epifluorescent microscopy was used to score a minimum of 100 cells per monolayer as being either Invaplex-positive or Invaplex-negative based on the presence or absence of cell-associated Invaplex-specific fluorescence, respectively. The mean number of cells counted and the mean number of fluorescent cells in duplicate monolayer treated in the same manner was reported.

Figure 11A:
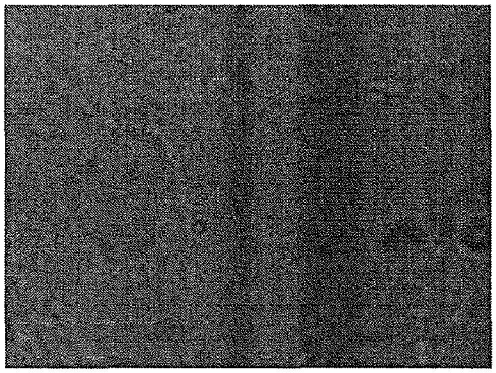
FIG. 11(A-F) show Invaplex-mediated transfection of plasmid DNA encoding 56k protein and transport of 56k protein intracellularly.
Figure 11B:
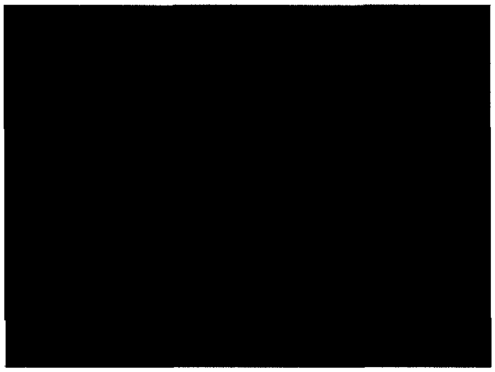
Figure 11C:
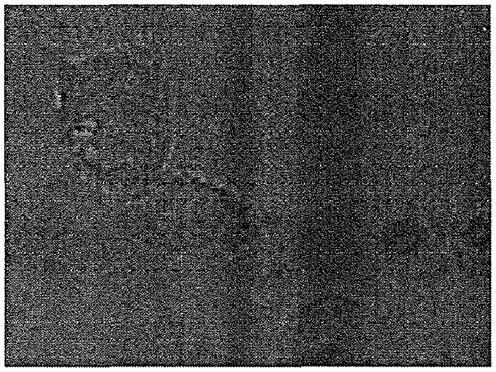
Figure 11D:
Figure 11E:
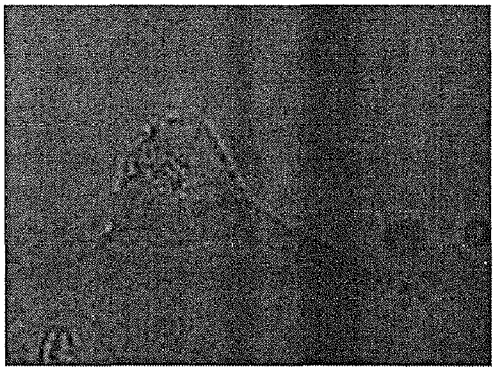
Figure 11F:

Invaplex-Mediated Transport of *Orientia tsutsugamushi* 56k Protein and Plasmid DNA Encoding Sta56k Protein Across Mammalian Cell Membrane In Vitro BHK-21 cells were incubated with r56k protein (FIGS. 11A and 11B) or plasmid DNA encoding the r56k protein and Invaplex 24 (FIGS. 11C and 11D) or r56k protein and Invaplex 24 (FIGS. 11E and 11F). Cells possessing r56k protein have a red fluorescence and were photographed using an Optiphot-2 microscope equipped with a 540 nm excitation filter at 100× magnification.

Results indicate Invaplex is able to facilitate the delivery of plasmid DNA encoding the 56k protein in transcriptionally active form to BHK-21 fibroblasts (FIGS. 11*c* and 11*d*). Furthermore, purified 56k protein can be translocated to the cytoplasm when incubated with BHK-21 cells in the presence of Invaplex (FIGS. 11*e* and 11*f*), but 56k protein does not cross cellular membranes in the absence of Invaplex (FIGS. 11*a* and 11*b*) nor does plasmid DNA encoding the 56k protein (data not shown).

A series of experiments were designed and executed to evaluate the ability of *Shigella* Invaplex to function as a mucosal adjuvant for DNA-based vaccines. Plasmid DNA encoding the sta56 protein was used.

The Sta56 protein from *Orientia tsutsugamushi* was used as a model antigen in the two as a model antigen in the two gene immunization animal experiments described [sic] below.

Functionality of *Shigella* Invaplex as a Mucosal Adjuvant for DNA-Based Vaccines Outlined Below. Plasmid DNA Encoding the sta56 Gene was Used as the DNA Vaccine Construct. Invaplex-Sta56 DNA Adjuvanticity Study.

Humoral Immunity

Figure 12:
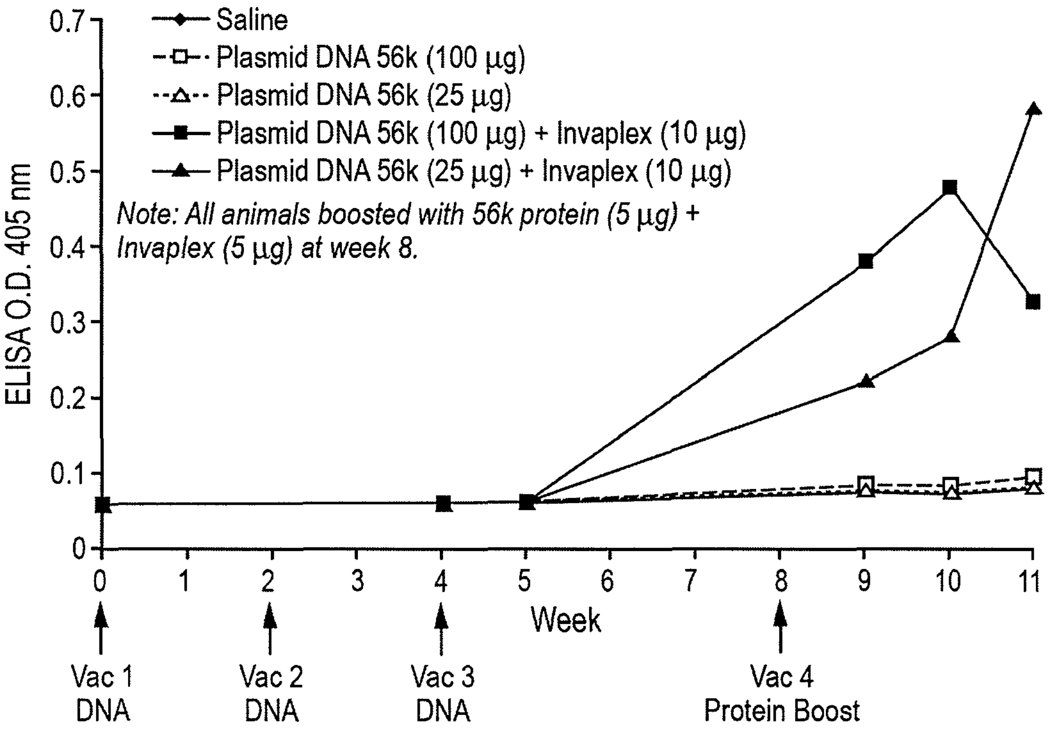
FIG. 12 shows Anti-56k protein serum IgG responses detected after DNA-Prime-Protein-Boost Strategy with Invaplex formulated vaccines.

After three immunizations with plasmid DNA (encoding the Sta56 protein) formulated with and without Invaplex, no detectable anti-Sta56K serum IgG responses were present at one or two weeks post the third immunization (FIG. 12). Immunization with DNA encoding Sta56 protein formulated with Invaplex and subsequently boosted once with purified r56K protein plus Invaplex elicited anti-Sta56 serum IgG responses with endpoints ranging from 1:360 to 1:1440. There was no anti-Sta56 serum IgG responses detectable after one immunization with the Sta56 protein (data not shown). Plasmid DNA immunization without Invaplex formulation did not substantially prime the humoral immune response as evidenced with no detectable anti-Sta56 antibody after protein boost. Combined, these results indicate that mucosal immunization with DNA formulated with Invaplex primed the humoral immune response to Sta56.

Cell-Mediated Immunity

Figure 13:
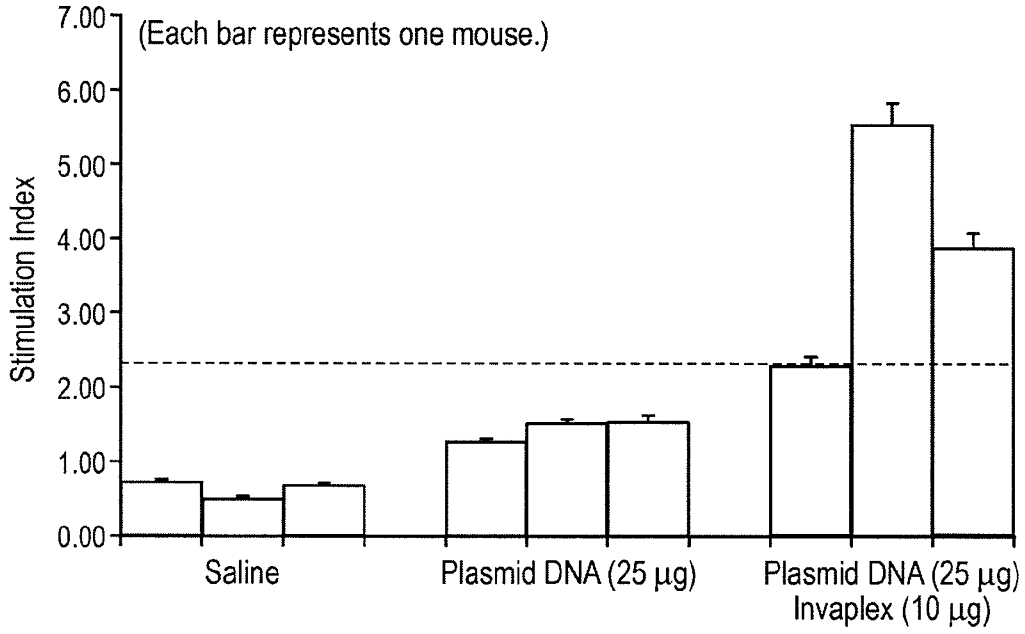
FIG. 13 shows Lymphoproliferative responses in splenocytes stimulated with r56k in vitro.

Significant antigen-specific proliferation was only detected in animals vaccinated with Invaplex formulated with plasmid DNA encoding the Sta56 protein. Plasmid DNA alone or saline control animals did not possess detectable proliferative responses when stimulated with Sta56 protein (FIG. 13).

Finally the appearance of Invaplex free in the cytoplasm at 60 minutes indicates that it has the ability to escape from the late endosomes or Golgi apparatus. Proteins or nucleic acids co-delivered with Invaplex would also be released into the host cell cytoplasm.

Functionality of *Shigella* Invaplex as a Mucosal Adjuvant for DNA-Based Vaccines: Invaplex-Sta56 DNA Adjuvanticity Study II The ability of *Shigella* Invaplex to enhance the immunogenicity of a plasmid DNA-based vaccine was evaluated in mice. Groups of female Balb/cByJ mice (10 mice/grp) were intranasally immunized on day 0, 14, and 28 with plasmid DNA containing the sta56 gene (25) from the Karp strain of *Orienta tsutsugamushi* linked to a cytomegalovirus (CMV) promoter (pVR1012_sta56). Mice were immunized with pVR1012_sta56 alone (25 or 100 μg) or pVR1012_sta56 combined with *S. flexneri* 2a Invaplex-50 (15 μg). Controls for the study included groups of mice intranasally immunized with either saline, *S. flexneri* 2a IVPlnvaplex-50 (15 μg) or the empty expression vector (pVR1012) (100 μg) combined with *S. flexneri* 2a Invaplex-50 (15 μg). Animals (5 mice/group) were boosted on day 56 with an intranasal immunization of purified recombinant Sta56 protein (15 μg) combined with *S. flexneri* 2a Invaplex-50 (5 μg). Animals were bled from the tail before vaccination on day 0 and day 28, and on days 35, 42, 56, 63, and 70. Cervical lymph nodes (CLN) and spleen cells were collected on day 70. Antigen-specific antibody responses were assessed in serum samples by an enzyme linked immunosorbant assay (ELISA) as previously described (27). Coating concentrations of the various antigens plated at 50 μl/well were: *S. flexneri* 2a Invaplex-50 (1 μg/ml) and the Sta56 protein (3 μg/ml). Splenocytes and cells from cervical lymph nodes were evaluated for antigen-specific proliferation using a colorimetric assay. Antigens used for proliferation included the Sta56 protein (20 μg/ml or 5 μg/ml) or *S. flexneri* 2a Invaplex-50 (5 μg/ml or 1 μg/ml).

Cell-Mediated Immune Responses Elicited with Plasmid DNA Encoding the Sta56 Protein from *O. tsutsugamushi* (pVR1012 56K) Delivered Alone or in Combination with *S. flexneri* 2a Invaplex-50

Figure 14A:
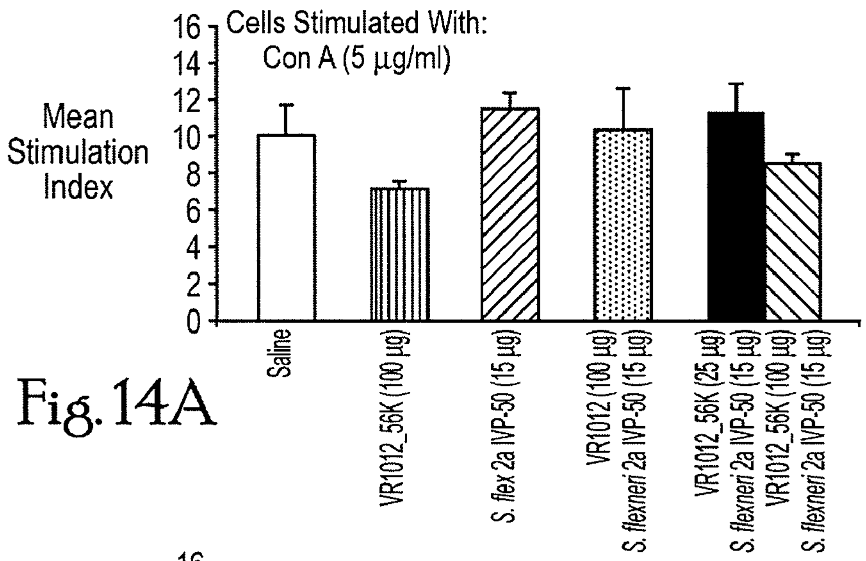
FIG. 14(A-C) show proliferative responses in murine splenocytes stimulated in vitro with Con A, *S. flexneri* 2a IVP-50 or Sta56 protein. Antigen-specific proliferation was measured after five days of culture using a non-radioactive cell proliferation assay. Data is expressed as the mean stimulation index of each vaccine group. Error bars represent ±1 SEM. A reference line denotes a stimulation index of 2. Vaccine groups are indicated on the horizontal axis.
Figure 14B:
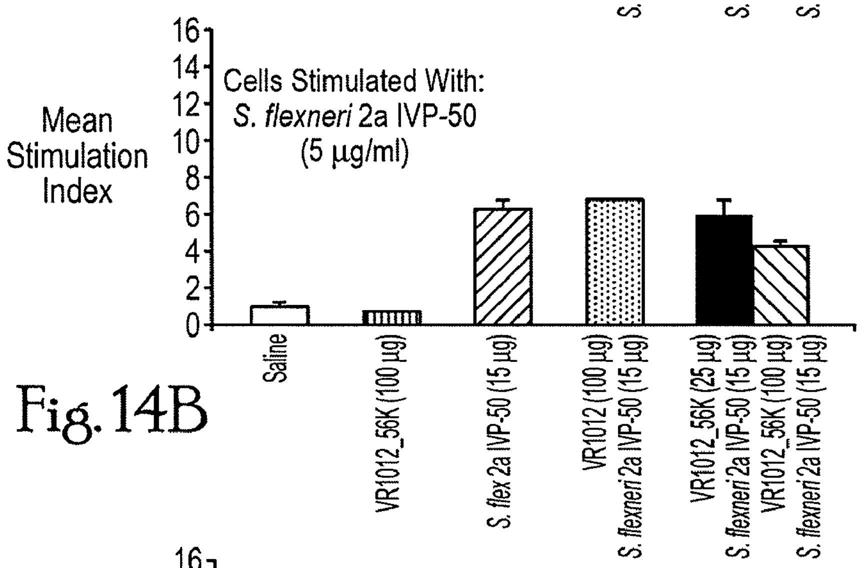
Figure 14C:
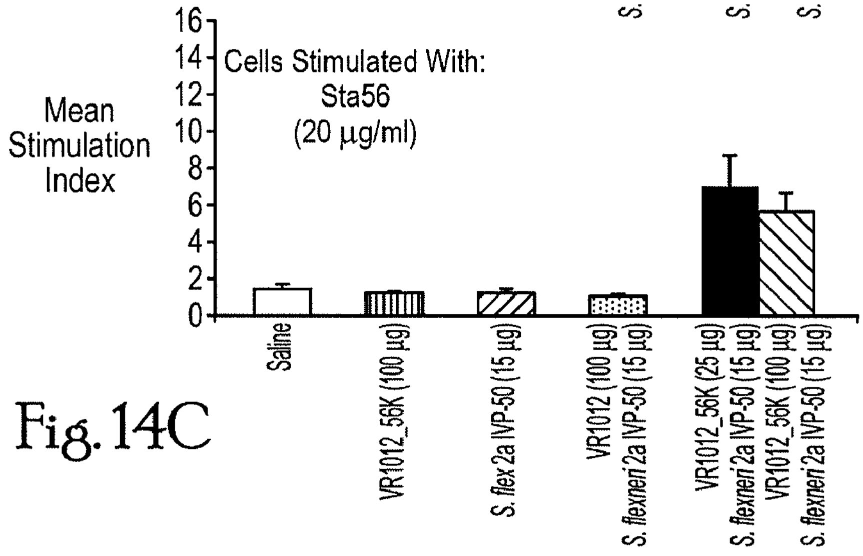

Spleens were harvested on day 42, two weeks after the third DNA immunization, from 5 mice of each treatment group. Antigen-specific (Sta56 and *S flexneri* 2a Invaplex-50) and mitogenic (Con A induced) proliferation was measured using a colorimetric proliferation assay. Whereas splenocytes from all animals from each treatment group proliferated in response to in vitro stimulation with Con A (FIG. 14, Top Panel), only animals immunized with pVR1012__56K combined with *S. flexneri* 2a Invaplex-50 proliferated after stimulation with purified, Sta56 protein (FIG. 14, Bottom Panel). The Sta56-specific proliferative response after immunization with pVR1012__56K (25 or 100 μg) combined with *S. flexneri* 2a Invaplex-50 was significantly higher ($p<0.002$) than the Sta56-specific proliferative responses detected after immunization with pVR1012__56K (100 μg) alone. The mean stimulation index (SI) in groups of mice immunized with pVR1012__56K (25 μg) combined with *S. flexneri* 2a IVP-50 was comparable ($p=0.12$) to the mean SI from mice immunized with pVR1012__56K (100 μg) combined with *S. flexneri* 2a Invaplex-50, indicating that intranasal immunization with higher amounts of pVR1012__56K combined with *S. flexneri* 2a Invaplex-50 did not result in higher levels of Sta56-specific proliferation (FIG. 14, Middle Panel).

Invaplex-Specific Proliferation in Splenocytes After Immunization with Plasmid DNA and Invaplex.

The Invaplex-specific proliferative responses were also measured after immunization with plasmid DNA and Invaplex. (FIG. 14, Middle Panel). Splenocytes isolated from mice immunized with *S. flexneri* 2a Invaplex-50 alone, or *S. flexneri* 2a Invaplex-50 combined with pVR1012 or *S. flexneri* 2a Invaplex-50 combined with pVR1012__56K proliferated after in vitro stimulation with *S. flexneri* 2a Invaplex-50, whereas no detectable Invaplex-specific proliferation was detected in groups immunized with saline or pVR1012__56K alone, further demonstrating the induction of Invaplex-specific cell-mediated immunity after immunization with *S. flexneri* 2a Invaplex-50.

Enhancement of Sta56-Specific Antibody Responses Elicited After *Shigella* Invaplex-Mediated Mucosal Delivery of Plasmid DNA-Based Vaccines In Vivo with an Invaplex-Sta56 Protein Booster Immunization.

Immunization with plasmid DNA encoding vaccine antigens has been previously shown to elicit primarily an antigen-specific T cell-mediated immune response and the generation of weak antigen-specific antibody responses (24). The enhancement of weak vaccine-specific antibody responses after DNA immunization has been previously accomplished by following the DNA vaccine regimen with a protein-based booster immunization (DNA prime-protein boost regimen) (24, 26).

Anti-Sta56 Serum Antibody Responses After Immunization with pVRIO12__56K Delivered Alone, or pVRIO12__56K Co-Delivered with *S. flexneri* 2a IVP-50 Followed by a Sta56 Protein-Invaplex Booster Immunization.

Intranasal immunization with saline on day 0, 14, and 28 followed by intranasal immunization with Sta56 protein (15 μg) combined with *S. flexneri* 2a Invaplex-50 (Invaplex-Sta56 protein) on day 56 did not result in the generation of detectable anti-Sta56 serum IgG responses (FIG. 15-A) indicating that one dose of Invaplex-Sta56 protein was not sufficient to mount a robust Sta56-specific humoral immune response. In contrast, groups of mice intranasally immunized three times with pVR1012__56K (either 25 or 100 μg) delivered with *S. flexneri* 2a Invaplex-50 (15 μg) followed by a single Invaplex-Sta56 protein booster immunization mounted a modest Sta56-specific serum IgG response detected one and two weeks after the protein booster immunization. The Sta56 specific serum IgG response elicited after intranasal immunization with pVR1012__56K (either 25 or 100 μg) delivered with *S. flexneri* 2a IVP-50 (15 μg) was significantly higher ($p<0.05$; unpaired T test) as compared to the Sta56-specific serum IgG response elicited after immunization with pVR1012__56K alone one and two weeks after the Invaplex-Sta56 protein booster immunization. Immunization with *S flexneri* 2a Invaplex-50 alone, or combined with pVR1012 (empty expression vector control) did not result in a detectable anti-StaS6 serum IgG response one or two weeks after the Invaplex-Sta56 protein boost, indicating that successful priming of the immune system with pVR1012__56K delivered with Invaplex was required for the subsequent Sta56-specific antibody response post-protein boost.

Anti-Invaplex Antibody Responses After Immunization with pVR1012__56K Delivered Alone, or pVR1012__56K Co-Delivered with *S. flexneri* 2a Invaplex-50 Followed by an Invaplex-Sta56 Protein Booster Immunization (Subgroup B).

The Invaplex-specific serum IgG responses were also assessed by ELISA (FIG. 15-B). Groups of mice immunized with saline or pVR1012__56K alone did not mount a detectable anti-Invaplex serum IgG response at any time point assayed, including one and two weeks after the single Invaplex-Sta56 protein boost. Groups of mice immunized with *S. flexneri* 2a delivered alone, or in combination with pVR1012 or pVR1012__56K (25 or 100 μg) mounted a robust anti-Invaplex serum IgG response, first detected one week after the third immunization (day 35). The anti-Invaplex serum response increased on day 42 and was subsequently boosted on day 63, one week after the Invaplex-Sta56 protein booster immunization to levels similar to those levels measured two weeks after the third immunization (day 42). The anti-Invaplex serum IgG responses, after the third immunization, were maintained at high levels, with modest decreases in the anti-Invaplex serum IgG responses over the one month period between the third and fourth immunization, indicating the generation of a robust anti-Invaplex response.

Collectively, the results of the Invaplex-56K DNA experiments demonstrate that three intranasal immunizations with *S. flexneri* 2a Invaplex-50 combined pVR1012__56K elicits a 56K-specific and Invaplex-specific cell-mediated immune response. Boosting of the immune response with an intranasal immunization consisting of Invaplex combined with Sta56 protein (DNA-prime, protein-booster immunization regimen) broadened the Sta56-specific immune response to include a modest anti-Sta56 serum IgG response combined with Sta56-specific cell-mediated immunity measured in splenocytes two weeks after the fourth immunization. Therefore, data from the second Invaplex Sta56 DNA Adjuvanticity study confirm previous results and indicate that *S. flexneri* 2a Invaplex-50 was capable of enhancing the immunogenicity of a plasmid-based DNA vaccine and acts as a mucosal adjuvant for DNA-based vaccines.

REFERENCES

1. Buysse, J. M., Stover, C. K., Oaks, E. V., Venkatesan, M., Kopecko, D. J. Molecular cloning of invasion plasmid antigen (ipa) genes from *Shigella flexneri*: Analysis of ipa gene products and genetic mapping. *J. Bacteriology,* 169: 2561-2569, 1987.
2. Davis, H. L. Plasmid DNA expression systems for the purpose of immunization. *Curr. Opin. Biotech.* 8:635-640, 1997.
3. DenisMize, K. S., Dupuis, M., MacKichan, M. L., et al. Plasmid DNA adsorbed onto cationic microparticles mediates target gene expression and antigen presentation by dendritic cells. *Gene Therapy* 7:2105-2112, 2000.
4. Gregoriadis, G., Bacon, A., Caparros-Wanderley, W., and McCormack, B. A role for liposomes in genetic vaccination. *Vaccine,* 20:B1-B9, 2002.
5. Grillot-Courvalin, C., Goussard, S., and Courvalin, P. Bacteria as gene delivery vectors for mammalian cells. *Curr. Opin. Biotech.* 10:477481, 1999.
6. Klavinskis, L. S., Gao, L., Barnfield, C. Lehner, T., and Parker, S. Mucosal immunization with DNA-liposome complexes. *Vaccine:* 15:818-820, 1997.
7. Menard, R., Sansonetti, P. J., and Parsot, C. Nonpolar mutagenesis of the ipa genes defines IpaB, IpaC, and IpaD as effectors of *Shigella flexneri* entry into epithelial cells. *J. Bacterial.,* 175:5899-5906, 1993.
8. Menard R., Sansonetti, P. J., and Parsot, C. The secretion of the *Shigella flexneri* Ipa invasins is activated by epithelial cells and controlled by IpaB and IpaD. *EMBO J.,* 13:5293-5302, 1994.
9. Mills, J. A., Buysse, J. M., and Oaks, E. V. *Shigella flexneri* invasion plasmid antigens B and C: Epitope location and characterization with monoclonal antibodies. *Infect. Immun.* 56:2933-2941, 1988.
10. Oaks, E. V., Hale, T. L., and Formal, S. B. The serum immune response against *Shigella* protein antigens in Rhesus monkeys and humans infected with *Shigella* spp. *Infect. Immun.* 53:57-63, 1986.
11. Oaks, E. V. and Turbyfill, K. R. Invaplex from gram negative bacteria, method of purification and methods of use. U.S. Pat. No. 6,245,892, issued Jun. 12, 2001.
12. Oaks, E. V., Turbyfill, K. R., and Hartman, A. B. Use of purified invasin complex from gram negative bacteria as a vaccine. U.S. Pat. No. 6,277,379, issued Aug. 21, 2001.
13. Oaks, E. V. and Turbyfill, K. R. Invaplex from gram negative bacteria, methods of purification and methods of use. U.S. Ser. No. 09/722,278, filing date Jan. 31, 2001.
14. Oaks, E. V. and Turbyfill, K. R. Heterologous Protection Induced by Immunization with the Invaplex Vaccine. U.S. patent application Ser. No. 10/150,814, filing date May 17, 2002 (PCT Application).
15. Rojas, M., Donahue, J. P., Tan, Z., and Lin, Y. Z. Genetic engineering of proteins with cell membrane permeability. *Nat. Biotech.* 16: 370-375, 1998.
16. Sansonnetti, P. J. Genetic and molecular basis of epithelial cell invasion by *Shigella* species. *Rev. Infect. Dis.* 13(Suppl 4): S285-292, 1991.

17. Schwarze, S. R., Ho, A., Vocero-Akbani, A., Dowdy, S. F. In vivo protein transduction: delivery of a biologically active protein into the mouse. *Science* 285:1569-1572, 1999.

18. Smith P K, Krohn R I, Hermanson G T, Mallia A K, Gartner F H, Provenzano M D, Fujimoto E K, Goeke N M, Olson B J, Klenk D C. 1985. Measurement of protein using bicinchoninic acid. *Anal Biochem*. October; 150(1):76-85.

19. Strober, 1994, Current Protocols in *Immunology, supplement* 11:7.10.1.

20. Turbyfill, K. R., Hartman, A. B., and Oaks, E. V. Isolation and characterization of a *Shigella flexneri* invasin complex subunit vaccine. *Infect. Immun.* 68:6624-6632, 2000.

21. Yoshida, A., Nagata, T., Uchijima, M., Higashi, T., Koide, Y. Advantage of gene gun-mediated over intramuscular inoculation of plasmid DNA vaccine in reproducible induction of specific immune responses. *Vaccine* 18:1725-1729, 2000.

22. Watarai, M., Tobe, T., Yoshikawa, M., and Sasakawa, C. Contact of *Shigella* with host cells triggers release of Ipa invasins and is an essential function of invasiveness. *EMBO J.,* 14:2461-2470, 1995.

23. Zelphati, O., Wang, Y., Kitanda, S., et al. Intracellular delivery of proteins with a new lipid-mediated delivery system. *J. Biol. Chem.* 276:35103-35110, 2001.

24. Habel, A., C. Chanel, R. Le Grand, F. Martinon, L. Couillin, C. Moog, R. Doms, M. C. Gauduin, B. Hurtrel, J. G. Guillet, A. M. Aubertin, and M. Girard, 2000: DNA vaccine protection against challenge with simian/human immunodeficiency virus 89.6 in rhesus macaques. *Dev Biol* (*Basel*), 104, 101-5.

25. Oaks, E. V., C. K. Stover, and R. M. Rice, 1987: Molecular cloning and expression of *Rickettsia tsutsugamushi* genes for two major protein antigens in *Escherichia coli. Infect Immun,* 55, 1156-62.

26. Terrazzini, N., S. Hannesdottir, P. J. Delves, and T. Lund, 2004: DNA immunization with plasmids expressing hCG-beta-chimeras. *Vaccine,* 22, 2146-53.

27. Turbyfill, K. R., A. B. Hartman, and E. V. Oaks, 2000: Isolation and characterization of a *Shigella flexneri* invasin complex subunit vaccine. *Infect Immun,* 68, 6624-32.

28. Mills I G, Jones A T, Clague M J. Involvement of the endosomal autoantigen EEA1 in homotypic fusion of early endosomes. *Curr Biol.* 1998 Jul. 16; 8(15):881-4.

29. Soldati T, Riederer M A, Pfeffer S R. Rab G D I: a solubilizing and recycling factor for rab9 protein. *Mol Biol Cell.* 1993 April; 4(4):425-34.

30. Dintzis S M, Velculescu V E, Pfeffer S R. Receptor extracellular domains may contain trafficking information. Studies of the 300-kDa mannose 6-phosphate receptor. *J Biol Chem.* 1994 Apr. 22; 269(16):12159-066.

31. Donaldson J G, Lippincott-Schwartz J, Bloom G S, Kreis T E, Klausner R D. Dissociation of a 110-kD peripheral membrane protein from the Golgi apparatus is an early event in brefeldin A action. *J Cell Biol.* 1990 December; 111(6 Pt 1):2295-306.

To the extent necessary to understand or complete the disclosure of the present invention, all publications, patents, and patent applications mentioned herein are expressly incorporated by reference therein to the same extent as though each were individually so incorporated.

The invention claimed is:

1. An in vitro process for transporting a compound of interest into a eukaryotic cell comprising contacting the eukaryotic cell with the compound and a sufficient amount of isolated Invaplex and for a time sufficient to cause the cell to take up the compound, wherein the Invaplex has the composition of either Invaplex 24 or Invaplex 50.

2. The in vitro process of claim 1 wherein the compound is an antibiotic, antibody, biopharmaceutical, hormone reporter molecule, enzyme or receptor.

3. The in vitro process of claim 1 wherein the compound is a carbohydrate, glycoprotein, lipid, lipopolysaccharide, polysaccharide, protein or peptide.

4. The in vitro process of claim 3 wherein the compound is a protein.

5. The in vitro process of claim 3 wherein the compound is a peptide.

6. The in vitro process of claim 1 wherein the cell is a tumor cell.

7. The in vitro process of claim 2 wherein the compound is an enzyme.

8. An in vivo process for transporting a compound of interest into eukaryotic cells of a subject comprising separately administering the compound and an effective amount of isolated Invaplex to the subject, wherein the Invaplex has the composition of either Invaplex 24 or Invaplex 50 and wherein the compound is a carbohydrate, glycoprotein, lipid, lipopolysaccharide, polysaccharide, protein or peptide and monitoring the presence of the compound within the cells.

9. The in vivo process of claim 8 wherein the compound is a protein.

10. The in vivo process of claim 9 wherein the compound is an enzyme.

11. The in vivo process of claim 8 wherein the compound is a peptide.

12. The in vivo process of claim 8 wherein the administration involves mucosal administration.

* * * * *